(12) United States Patent
Gierhart

(10) Patent No.: US 7,941,211 B2
(45) Date of Patent: May 10, 2011

(54) PRELOADING WITH MACULAR PIGMENT TO IMPROVE PHOTODYNAMIC TREATMENT OF RETINAL VASCULAR DISORDERS

(75) Inventor: Dennis L. Gierhart, Chesterfield, MO (US)

(73) Assignee: ZeaVision, LLC., Chesterfield, MO (US)

( * ) Notice: Subject to any disclaimer, the term of this patent is extended or adjusted under 35 U.S.C. 154(b) by 1713 days.

(21) Appl. No.: 10/972,699

(22) Filed: Oct. 23, 2004

(65) Prior Publication Data

US 2005/0171212 A1 Aug. 4, 2005

Related U.S. Application Data

(60) Provisional application No. 60/523,179, filed on Nov. 17, 2003.

(51) Int. Cl.
A61N 1/30 (2006.01)
A01N 35/00 (2006.01)
A61K 31/12 (2006.01)

(52) U.S. Cl. .......................................... 604/20; 514/690

(58) Field of Classification Search .................. 514/690; 604/20

See application file for complete search history.

(56) References Cited

U.S. PATENT DOCUMENTS

| | | | |
|---|---|---|---|
| 3,841,967 A | 10/1974 | Dasek et al. | 195/29 |
| 3,879,424 A | 4/1975 | Surmatis et al. | 260/340.9 |
| 3,891,504 A | 6/1975 | Schocher et al. | 195/28 R |
| 3,920,834 A | 11/1975 | Klaui et al. | 424/305 |
| 3,932,462 A | 1/1976 | Goetz et al. | 260/340.7 |
| 3,951,743 A | 4/1976 | Shepherd et al. | 195/28 R |
| 3,954,804 A | 5/1976 | Fischer et al. | 260/340.7 |
| 3,974,181 A | 8/1976 | Surmatis et al. | 260/340.9 |
| 4,078,094 A | 3/1978 | Katzen | 426/641 |
| 4,153,615 A | 5/1979 | Saucy | 260/340.9 R |
| 4,298,621 A | 11/1981 | Samis et al. | 426/55 |
| 4,405,417 A | 9/1983 | Grass et al. | 204/73 R |
| 4,522,743 A | 6/1985 | Horn et al. | 252/311 |
| 4,579,973 A | 4/1986 | Widmer et al. | 568/347 |
| 4,726,955 A | 2/1988 | Horn et al. | 426/73 |
| 4,851,339 A | 7/1989 | Hills | 435/67 |
| 4,935,409 A | 6/1990 | Wollweber et al. | 514/63 |
| 4,952,716 A | 8/1990 | Lukac et al. | 556/482 |
| 5,180,747 A | 1/1993 | Matsuda | 514/681 |
| 5,227,507 A | 7/1993 | Lukac et al. | 556/449 |
| 5,242,950 A | 9/1993 | Hastings | 514/654 |
| 5,290,605 A | 3/1994 | Shapira | 424/439 |
| 5,308,759 A | 5/1994 | Gierhart | 435/67 |
| 5,310,764 A | 5/1994 | Baranowitz et al. | 514/725 |
| 5,350,773 A | 9/1994 | Schweikert et al. | 514/763 |
| 5,356,636 A | 10/1994 | Schneider et al. | 424/489 |
| 5,360,730 A | 11/1994 | Orndorff et al. | 435/257.1 |
| 5,382,714 A | 1/1995 | Khachik | 568/834 |
| 5,386,063 A | 1/1995 | Khachik et al. | 568/494 |
| 5,427,783 A | 6/1995 | Gierhart | 424/93.4 |
| 5,429,939 A | 7/1995 | Misawa et al. | 435/67 |
| 5,437,997 A | 8/1995 | Liao et al. | 435/257.1 |
| 5,523,494 A | 6/1996 | Torres-Cardona et al. | 568/834 |
| 5,527,533 A | 6/1996 | Tso et al. | 424/422 |
| 5,607,839 A | 3/1997 | Tsubokura et al. | 435/67 |
| 5,684,238 A | 11/1997 | Ausich et al. | 800/205 |
| 5,777,173 A | 7/1998 | Paust et al. | 568/366 |
| 5,780,693 A | 7/1998 | Bernhard et al. | 568/816 |
| 5,871,766 A | 2/1999 | Hennekens | 424/422 |
| 6,218,436 B1 | 4/2001 | Howard et al. | 514/725 |
| 6,443,976 B1* | 9/2002 | Flower et al. | 607/88 |
| 2003/0002014 A1* | 1/2003 | Grant | 351/221 |
| 2004/0087664 A1* | 5/2004 | Marcus et al. | 514/691 |
| 2004/0176345 A1* | 9/2004 | Lavie | 514/185 |

FOREIGN PATENT DOCUMENTS

EP 0 747 483 A2 12/1996
WO WO 96/40092 A1 12/1996

OTHER PUBLICATIONS

Thomas Ciulla, et al, Changing Therapeutic Paradigms for Exudative Age-related Macular Degeneration: Antiangiogenic Agents and Photodynamic Therapy, 8 Exp. Opin. Invest. Drugs 2173 (1999).*
Paul Bernstein & Nikita Katz, The Role of Ocular Free Radicals in Age-Related Macular Degeneration, 20 Cut. Ocular Toxicol. 141, 163-73 (2001).*
D.W. Harkin, et al, Reperfusion Injury is Greater with Delayed Restoration of Venous Outflow in Concurrent Arterial and Venous Limb Injury, 87 Br. J Surg. 734 (2000).*
Bendich, A., et al, "Biological actions of carotenoids," FASEB Journal 3: 1927-1932 (1989).
Bone, R.A., et al, "Preliminary identification of the human macular pigment," Vision Res. 25: 1531-1535 (1985).
Bone R.A., et al, "Stereochemistry of the macular carotenoids," Invest. Ophthalmol. Vis. Sci. 34: 2033-2040 (1993).
Columbo, V.E., et al, "Structures and properties of stabilized vitamin and carotenoid dry powders," Food Structure 10: 161-170 (1991).

(Continued)

*Primary Examiner* — Jeffrey S. Lundgren
*Assistant Examiner* — Sean Basquill
(74) *Attorney, Agent, or Firm* — Nixon Peabody LLP

(57) ABSTRACT

Pre-treatment using a xanthin carotenoid (preferably 3R,3'R-zeaxanthin) can improve the benefits and efficacy of photodynamic therapy (PDT), which uses a light-activated drug (such as verteporfin) in patients who suffer from unwanted retinal blood vessel growth, including the "wet" (exudative) form of macular degeneration. Before a PDT treatment, patients are given a regimen of orally-ingested zeaxanthin for a period of at least 1 and preferably at least 2 to 3 weeks, at dosages of at least 3 and preferably at least 10 milligrams per day. Since zeaxanthin imparts a yellowish color to the macula, a preferred dosage should increase a patient's macular pigment density before the PDT treatment is performed.

12 Claims, 3 Drawing Sheets

OTHER PUBLICATIONS di Mascio, P., et al, "Lycopene as the most efficient biological carotenoid singlet oxygen quencher," Archives of Biochemistry and Biophysics 274: 532-538 (1989).
di Mascio, P., et al, "Antioxidant defense systems: the role of carotenoids, tocopherols, and thiols," Am. J. Clin. Nutr. 53: 194S-200S (1991).
Dorey, C.K., et al, "Lipofuscin in aged and AMD eyes," in Retinal Degeneration (Hollyfield et al., editors, Plenum Press, New York, 1993).
Eye Disease Case Control Study Group, "Antioxidant status and neovascular age-related macular degeneration," Arch. Ophthalmol. 11: 104-109 (1993).
Gerster, H., "Review: antioxidant protection of the aging macula," Age and Aging 20: 60-69 (1991).
Haegerstrom-Portnoy, G., "Short-wavelength-sensitive-cone sensitivity loss with aging: a protective role for macular pigment?," J. Opt. Soc. Am. A5: 2140-2144 (1988).
Handelman, G.J. and Dratz, E.A., "The role of antioxidants in the retina and retinal pigment epithelium and the nature of prooxidant-induced damage," Adv. in Free Radical Biology & Medicine 2: 1-23 and 55-57 (1986).
Handelman, G.J., et al, "Carotenoids in the human macula and whole retina," Invest. Ophthalmol. Vis. Sci. 29: 850-855 (1988).
Malinow, M.R., et al, "Diet-related macular anomalies in monkeys," Invest. Ophthalmol. Vis. Sci. 19: 857-863 (1980).
National Advisory Eye Council, Vision Research: A National Plan, 1994-1998 (NIH Publication 93-3186), pp. 55-64, 336, and 356(1998).
Seddon, J.M., et al, "Dietary carotenoids, vitamins A, C, and E, and advanced age-related macular degeneration," JAMA 272: 1413-1420 (1994).
Sperduto, R.D., et al, "Do we have a nutritional treatment for age-related cataract or macular degeneration?," Arch. Ophthalmol. 108: 1403-1405 (1990).
Taylor, A., et al, "Oxidation and aging: impact on vision," Journal of Toxicology and Industrial Health 9:349-371 (1993).
"Flora-Glo Lutein" product specification sheets (Kemin Industries Inc., Des Moines, Iowa, 1997).
Alpers, J.R., et al, "Serum Carotenoids and Age-Related Macular Degeneration," Invest Ophthalmol Vis Sci 36: S9 (1995).
Ascherio, A., et al, "Correlations of Vitamin A and E Intakes with the Plasma Concentrations of Carotenoids and Tocopherols among American Men and Women," J of Nutrition 122 (9): 1792-1801 (1992).
Bertram, J.S., et al, "Diverse carotenoids protect against chemically induced neoplastic transformation," Carcinogenesis 12 (4): 671-678 (1991).
Blumenkranz, M.S., et al, "Risk factors in age-related maculopathy complicated by choroidal neovascularization," Ophthalmology 93: 552-558 (1986).
Bone, R.A., et al, "Distribution of macular pigment stereomers in individual eyes, including those with age-related macular degeneration (AMD)," Arvo Abstracts Invest Ophthalmol Vis Sci V.35: 4 pp 1502 (1994).
Bone, R.A., et al, "Analysis of the macular pigment by HPLC: retinal distribution and age study," Invest Ophthalmol Vis Sci 29: 843-9 (1988).
Bone, R.A., "The role of the macular pigment in the detection of polarized light," Vision Research 30: 213-220 (1979).
Bowmaker, J.D., et al, "Visual pigments and oil droplets in genetically manipulated and carotenoid deprived quail: a microspectrophotometric study," Vision Res 33: 571-578 (1993).
Burton, G.W., "Antioxidant action of carotenoids," American Institute of Nutrition, 109-111 (1988).
Castorina, C., et al, "Lipid peroxidation and antioxidant enzymatic systems in rat retina as a function of age," Neurochem Res 17(6): 599-604 (1992).
Christen, W.G., "Antioxidants and eye disease," The Amer J of Medicine 97 (suppl 3A): 3A-142-3A-162 (1994).
Conn, P.F., et al, "The singlet oxygen and carotenoid interaction," J Photochem Photobiol B Biol 11: 41-47 (1991).

Crary, E.J., "Antioxidant treatment of macular degeneration of the aging and macular edema in diabetic retinopathy," Southern Med J 80: 38 (1997).
Fite, K.V., "Drusen-like deposits in the outer retina of Japanese quail," Exp Eye Res 59: 417-424 (1994).
Fite, K.V., et al, "Experimental light damage increases lipofuscin in the retinal pigment epithelium of Japanese quail," Exp Eye Res 57: 449-460 (1993).
Fite, K.V., et al, "Age, sex and light damage in the avian retina: a model system," P. Bagnoli et al, Ed, The Changing Visual System: 283-294 (1991).
Foote, C.S., et al, "Chemistry of singlet oxygen. X. Carotenoid quenching parallels biological protection," J Amer Chem Soc 92: 17 (1970).
Goldberg, J., et al, "Factors Associated with Age-Related Macular Degeneration: An analysis of Data from the First National Health and Nutrition Examination Survey," Am J Epidemiol 128(4): 700-10 (1988).
Gottsch, J.D., et al, "Hematogenous photosensitization," Inves Opthamol & Vis Sci 31(9): 1674-1682 (1990).
Gruszecki, W.I., et al, "Orientation of xanthophylls in phosphatidylcholine multibilayers," Biochim Biophys Acta 1023(3): 405-412 (1990).
Ham, W.T., et al, "Basic mechanisms underlying the production of photochemical lesions in the mammalian retina," Curr Eye Res 3(1): 165-174 (1984).
Ham, W.T., et al, "The photopathology and nature of the blue-light and near-UV retinal lesions produced by lasers and other optical sources," ed. Plenum Press; New York, Laser Application in Medicine and Biology: 191-246 (1989).
Hockwin, O., et al, "Investigations on lens transparency and its disturbances by microdensitometric analyses of Scheimpflug photographs," Curr Eye Res 3(1): 15-22 (1984).
Hope, G.M., et al, "A primate model for age related macular drusen," British J of Ophthalmol 76: 11-16 (1992).
Kahn, H.A., et al, "Framingham Eye Study 1. Outline and major prevalence finding," Am J Epidemiol 106(1): 17-32 (1977).
Khachik, F., et al, "Lutein, lycopene, and their oxidative metabolites in chemoprevention of cancer," J of Cell Biochem S22: 236-246 (1995).
Khachik F., et al, "Separation and identification of carotenoids and their oxidation products in the extracts of human plasma," Anal Chem 64: 2111-22 (1992).
Kirschfeld, K., "Carotenoid pigments: their possible role in protecting against photooxidation in eyes and photoreceptor sells," Proc R Soc London B 216: 71-85 (1982).
Klaui, H. and Bauerenfeind, C.J., pp. 86-102 in Carotenoids as colorants and vitamin A precursors, Baurenfeind, C.J., Ed, Academic Press (1981).
Klein, R., et al, "Racial/ethnic differences in age-related maculopathy. Third National Health and Nutrition Examination Survey," Opthamology 102(3): 371-81 (1995).
Klein, B., et al, "Prevalence of Age-related Lens Opacities in a Population: The Beaver Dam Eye Study," Ophthalmol 99(4): 546-52 (1992).
Mangels, A.R., et al, "Carotenoid content of fruits and vegetables: an evaluation of analytical data," J Amer Diet Assn 93(3): 284-96 (1993).
Mares-Perlman, J.A., et al, "Serum antioxidants and age-related macular degeneration in a population-based case-control study," Arch Ophthalmol 113: 1518-1523 (1995).
Monaco, W.A., et al, "The rhesus monkey as an animal model for age-related maculopathy," Optometry Vis Sci 67(7): 532-537 (1990).
Nussbaum, J.J., et al, "Historic perspectives Macular yellow pigment. The first 200 years," Ophthal Comm Soc 1(4): 296-310 (1981).
Parker, R.S., "Carotenoids in human blood and tissues," Amer Inst Nutr: 101-104 (1988).
Pease, P.L., et al, "Optical density of human macular pigment," Vis Res 27(5): 705-710.
Sanders, T.A.B., et al, "Essential fatty acids, plasma cholesterol, and fat-soluble vitamins in subjects with age-related maculopathy and matched control subjects," Am J Clin Nutr 57: 428-433 (1993).

Schalch, W., "Carotenoids in the retina—a review of their possible role in preventing or limiting damage caused by light and oxygen," Emerit I., et al, Ed, Free Radicals and Aging: 280-298 (1992).

Seddon, J.M., et al, "Vitamins, minerals, and macular degeneration: Promising but unproven hypotheses," Arch Ophthalmol 112: 176-179 (1994).

Snodderly, D.M., "Evidence for protection against age-related macular degeneration by carotenoids and antioxidant vitamins," Am J Clin Nutr 62(Suppl): 1448S-61S (1995).

Snodderly, D.M., et al, "The macular pigment. I. Absorbance spectra, localization, and discrimination from other yellow pigments in primate retinas," Invest Ophthalmol Vis Sci 25: 660-673 (1984a).

Snodderly, D.M., et al, "The macular pigment. II. Spatial distribution in primate retinas," Invest Ophthalmol Vis Sci 25: 674-85 (1984b).

Snodderly, D.M., et al, "Distribution of individual macular pigment carotenoids in central retina of macaque and squirrel monkeys," Invest Ophthalmol Vis Sci 32(2): 268-279 (1991).

Stone, W.L., et al, "A reinvestigation of the fatty acid content of bovine, rat and frog retinal rod outer segments," Exp Eye Res 28: 387-397 (1979).

Taylor, H.R., et al, "The long-term effects of visible light on the eye," Arch Ophthalmol 110: 99-104 (1992).

Thylefors, B., et al, "Global Data on Blindness," Bulletin of the World Health Organization 73(1): 115-121 (1995).

Vingerling, J.R., "Epidemiology of age-related maculopathy," Epidemiol Rev 17(2): 347-360 (1995).

Weiser, J., et al, "Provitamin A activities and physiological functions of carotenoids in animals: relevance to human health," Ann NY Acad Sci 691: 213-215 (1993).

Weiter, J.J., et al, "Central sparing in annular macular degeneration," Am J Ophthalmol 106: 286-292 (1988).

Werner, J.S., "Aging and human macular pigment density," Vis Res 27(2): 257-268 (1987).

West, S., et al, "Epidemiology of risk factors for age-related cataracts," Survey Ophthalmol 39(4): 323-34 (1995).

West, S., et al, "Are antioxidants or supplements protective for age-related macular degeneration?," Arch Ophthalmol 112: 222-227 (1994).

National Eye Advisory Council, pp. 13-38 in Vision Research—A National Plan: 1999-2003 (NIH Publ. 99-4120, 1999).

Jampol, L.M., "Antioxidants, zinc, and age-related macular degeneration," Arch Ophthalmol 119: 1533-1534 (2001).

AREDS Research Group, Report No. 8, "A randomized, placebo-controlled, clinical trial of high-dose supplementation with vitamins C and E, beta carotene, and zinc for age-related macular degeneration and vision loss," Arch Ophthalmol 119: 1417-1436 (2001).

Widmer et al, "Technical Procedures for the Synthesis of Carotenoids and Related Compounds from 6-Oxo-Isophrone: Synthesis of (3R-3'R) Zeaxnathin" Helvetica Chemica Acta, 73, 861-867 (1990).

"Do Antioxidants prevent or Retard the Onset of AMD?", J. Amer. Osteopathic Assn. 95(1): 26 (Jan. 1995).

"The Effect of a Dietary Lack of Xanthophyll on the Eye of the Monkey," *Nutrition Reviews* 38: 384-386 (1980).

Landrum, J.T., et al, "Macular Pigment Stereomers in Individual Eyes: A Comparison Between Normals and Those With Age-Related Macular Degeneration" (abstract), *Invest. Opthalm. Visual Sci.* 36(4): S895 (Conference Proceedings, Mar. 15, 1995).

Hammond, B.R., "The Relationship Between Cigarette Smoking and Peak Macular Pigment Density," *Invest. Opthalm. Visual Sci.* 36(4): S233 (Conference Proceedings, Mar. 15, 1995).

* cited by examiner

Beta-carotene -- no oxygen atoms, not a "xanthin" carotenoid 3R,3'R-zeaxanthin -- entirely symmetric, beta rings at both ends S,R ("meso") zeaxanthin -- not symmetric, hydroxy group at one end points down, never found in diet or blood Lutein -- "epsilon" end ring has non-conjugated sequence, no electron cloud to absorb UV or radicals

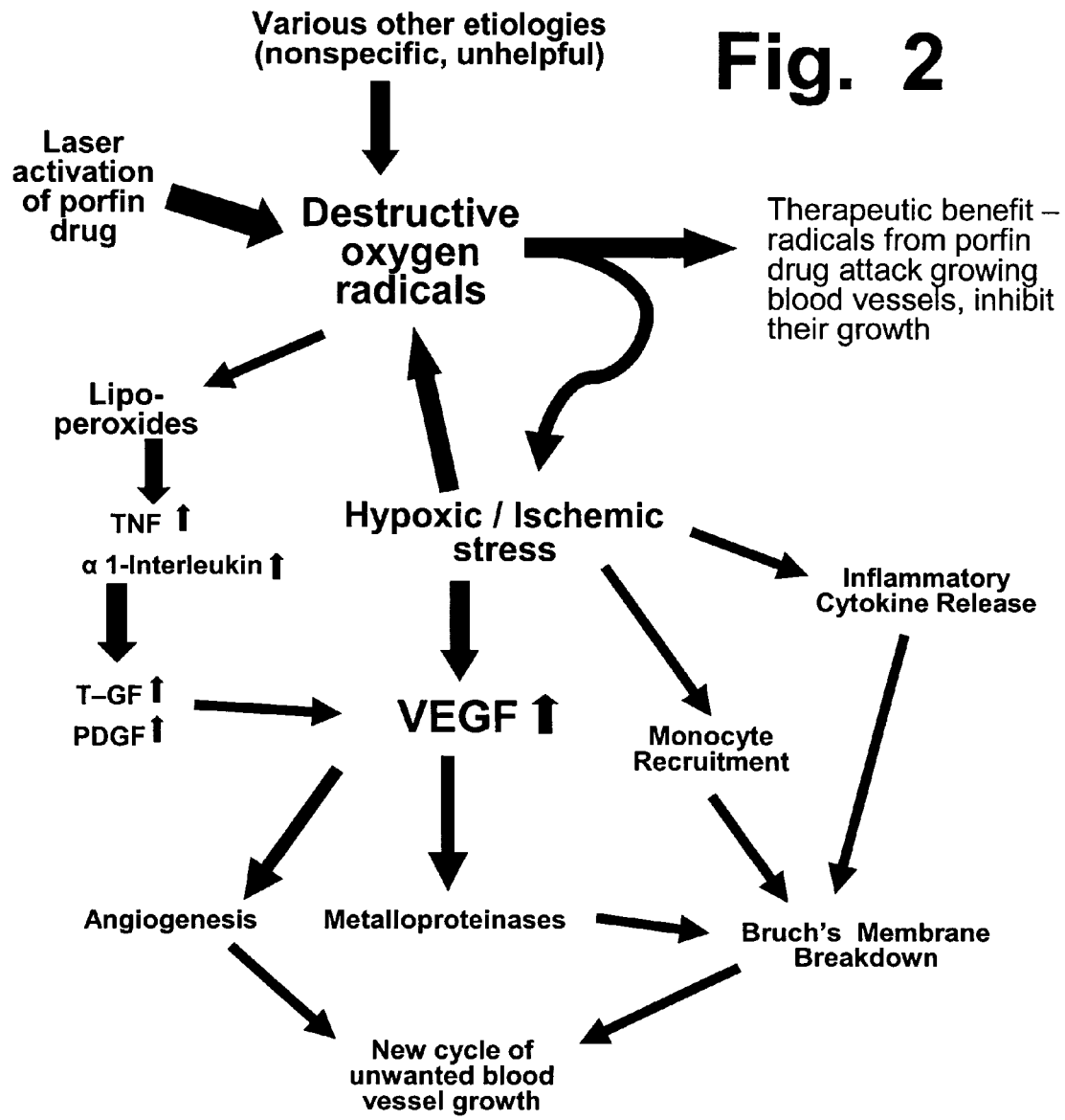

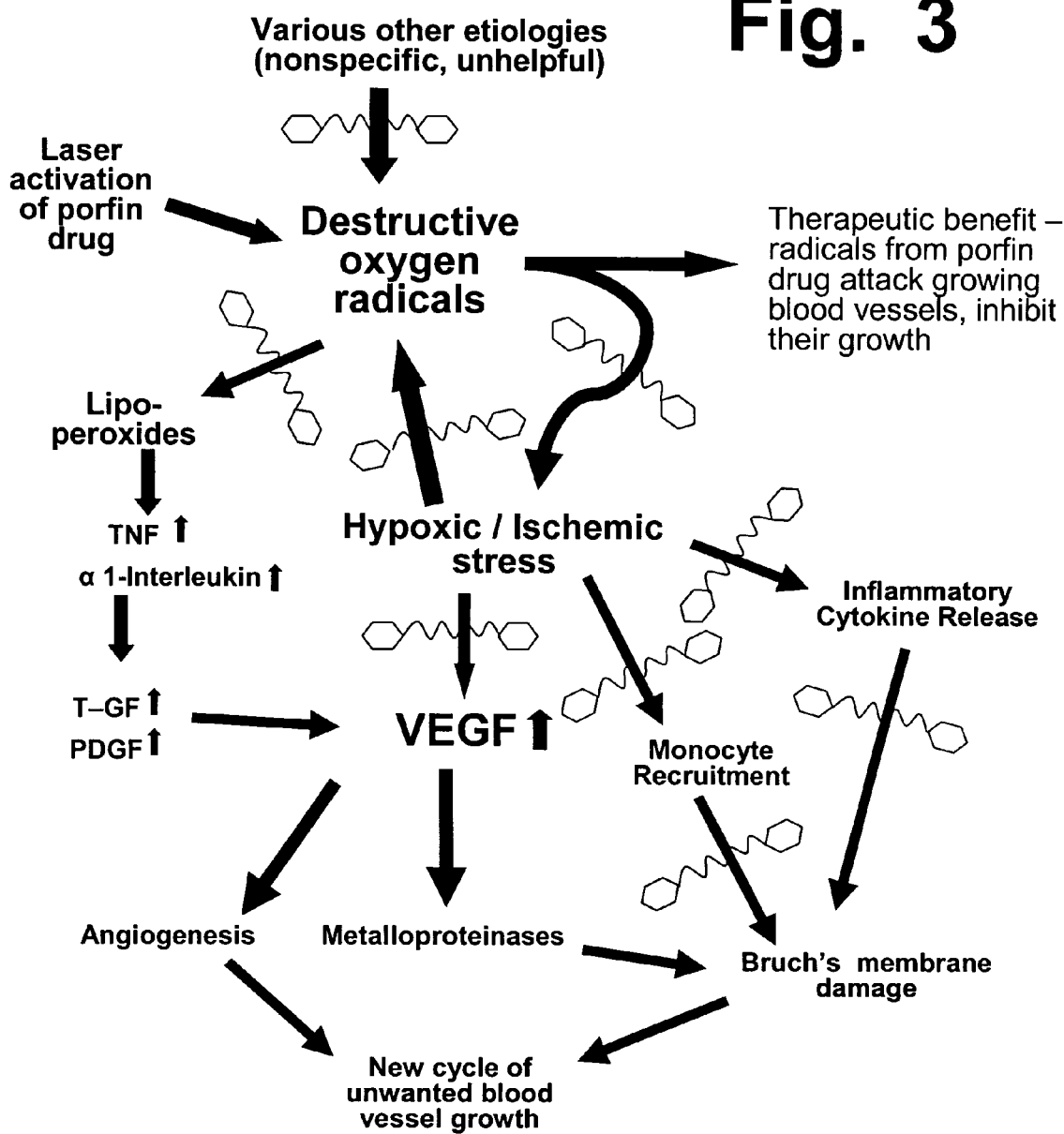

PRELOADING WITH MACULAR PIGMENT TO IMPROVE PHOTODYNAMIC TREATMENT OF RETINAL VASCULAR DISORDERS

RELATED APPLICATION

The Applicant claims priority, under 35 USC 119(e), based on provisional application No. 60/523,179, filed on Nov. 17, 2003.

FIELD OF THE INVENTION

This invention is in the field of medicine, and relates to administering a natural carotenoid pigment called zeaxanthin to patients who receive treatment using light-activated drugs to inhibit the unwanted growth of blood vessels in their retinas.

BACKGROUND OF THE INVENTION

The invention herein relates to certain types of medical treatments that use a laser-activated drug to slow down the growth of unwanted blood vessels in or behind the retina. This type of treatment can be used to treat a number of known eye and vision disorders, including:
  (i) the "wet" form of macular degeneration, discussed in more detail below;
  (ii) "proliferative diabetic retinopathy", a term used when these types of problems occur in people who suffer from diabetes;
  (iii) tissue responses that arise after an injury, infection, or inflammation, which are often given diagnostic labels, such as punctate inner choroidopathy, presumed ocular histoplasmosis syndrome, or multifocal choroiditis with panuveitis, as described in Wachtlin et al 2003.

The medical term choroidal neo-vascularization is also used to describe unwanted blood vessel growth affecting the retina. The choroid is a specialized layer of structural tissue, near the back of the eye, which is interlaced with capillaries; vascular refers to blood vessels, and neo-vascular refers to the growth of new blood vessels that previously were not present in a certain tissue (this is distinct from re-vascularization, which refers to the re-growth of blood vessels that were disrupted by an injury).

The labels listed above overlap heavily, and often can be used interchangeably. For example, since the macula is part of the retina, any case of "macular degeneration" is also, by definition, a "retinopathy" (i.e., a pathological condition affecting the retina).

The discussion below focuses on "wet" macular degeneration as an exemplary form of the group of eye diseases and disorders that can be treated by photodynamic therapy, using a drug-and-laser combination as described below. This description is intended to be illustrative, rather than limiting, and the methods disclosed herein should improve the benefits and outcomes for at least some patients having any particular type of retinal problem that will require treatment by photodynamic therapy (PDT).

Since it is a descriptive label, the term macular degeneration can include any eye or vision disorder that involves degeneration of the macula, a small yellowish-colored circular area in the center of the retina. This includes degeneration that may be caused or aggravated by other factors, such as diabetes, a genetic disorder, a vitamin deficiency, senescence, etc. "Degeneration" implies gradual and progressive deterioration, but this can include degeneration following an injury, infection, etc. Review articles that describe the etiology, pathology, and current treatments for macular degeneration include Ambati et al 2003 and Zarbin 2004.

In primates (including humans), which are the only mammals that have maculas, the macula is crucial to clear vision. Because of how the eyes and brains of primates evolved interactively, the macula is the only portion of the retina that provides fine-resolution vision, and the remainder of the retina provides only coarse-resolution vision. This limits and controls the number of nerve impulses that must be rapidly processed by the brain to provide clear and rapid-response vision, and it reduces the burden on the retina to continually regenerate and recycle huge numbers of replacements for the rod and cone structures, which are the light-activated portions of retinal neurons.

However, since the macula is extremely complex and highly sensitive, it sometimes encounters serious problems. Because it is the only part of the retina that provides clear and sharp vision, if it degenerates seriously, people with macular degeneration often completely lose the ability to read, drive, recognize faces, or carry out numerous other tasks. Macular degeneration is the leading cause of blindness among the elderly, and its occurrence rates are increasing as the population ages, and as people eat more prepared and fatty foods, and fewer fruits and dark green vegetables.

Some cases that arise before the age of about 50 involve known genetic problems, including disorders and syndromes such as Stargardt's disease, Best's disease, Batten's disease, Sjogren-Larsson syndrome, cone-rod dystrophy, ovine ceroid lipofuscinosis, and various genetic defects involving problems with mitochondria or lysosomes; in addition, diabetics suffer from elevated risks of diabetic retinopathies, most of which involve degeneration of the macula. However, other than genetic or diabetic cases, the vast majority of macular degeneration cases do not become noticeable until someone is past the age of about 60. These cases often are called age-related macular degeneration (often abbreviated as AMD or ARMD).

Regardless of whether they are genetic, diabetic, or age-related, cases of macular degeneration are usually divided into two main categories, depending on the types of physiological symptoms they display. If abnormal blood vessel growth in and/or behind the macula is involved, that eye will be diagnosed as having the wet form (sometimes called the exudative form). If abnormal blood vessel growth is not involved, the term dry macular degeneration is commonly used. While genetic or diabetic cases of macular degeneration tend to cause relatively consistent and similar damage in both eyes, it is common for cases of age-related macular degeneration to be manifested as the wet form in one eye, and the dry form in the other eye.

Abnormal blood vessel growth, in and/or behind the macula, can severely disrupt clarity of vision. Because of evolutionary factors, the blood vessels that serve most of the retina actually sit on the anterior (front) side of the retina. As mentioned above, most of the retina provides only coarse-resolution vision, so this arrangement does not disrupt normal eyesight.

However, as mentioned above, primates evolved with retinas that are more complex and sophisticated than in other mammals, and in primates, a fine-resolution macular region evolved at the crucially important center of their retinas. In that small but crucial part of the retina, the placement of blood vessels is reversed, and the blood vessels are positioned behind the retina, in the layer known as the choroid.

Unfortunately, that arrangement causes the macula to become seriously disrupted, if new and unwanted blood vessels in the supporting choroidal layer begin growing and proliferating in uncontrolled ways, directly behind and beneath the macula. When someone begins to suffer from wet macular degeneration, it becomes obvious to that person, in a fairly rapid manner, that their central vision is becoming blurry, and losing clarity. The person becomes unable to focus clearly, even if he or she stops doing anything else and tries hard to look at something.

Although the causes of abnormal blood vessel proliferation in wet macular degeneration are not entirely understood, it is generally presumed that one or more triggering and aggravating factors begin to inflict damage and stress on the cells and membranes of the macula, and the macula responds to the damage and stress by sending out hormonal signals that will recruit more blood flow, to try to help the system. This is a conventional and normal physiological response, since increased blood flow to tissues that are releasing stress-induced hormones will, in most cases, provide more nutrients, and improve waste removal, both of which are usually beneficial.

However, because of the arrangement of the tissue layers and blood vessels behind the macula, an increase in blood vessel growth at that particular location causes more damage than good. That additional damage increases, rather than decreases, the level of stress on the macular tissues, and an out-of-control feedback loop (which can be called a "vicious circle") begins to trigger even more aggressive blood vessel growth. Unwanted blood vessels begin growing even more rapidly, trying to cope with increasing levels of stress and damage in and around the macula, but the unwanted blood vessel growth makes the problems even worse. This leads to still more distress hormones being released by stressed and dying retinal cells, and those hormones trigger the growth of even more blood vessels.

As a result, wet (exudative) macular degeneration is highly aggressive. It spreads at relatively high rates, and it inflicts severe damage to the eyesight, often leading to functional blindness within a matter of months, compared to the slower progression of dry macular degeneration, which often takes years.

Even though the wet form of macular degeneration accounts for only about 5 to 15% of all cases of macular degeneration (estimates vary, because borderline cases often occur that are difficult to classify as either clearly wet, or clearly dry), it receives an inordinate amount of attention, compared to dry macular degeneration, for two reasons. First, the wet form is highly aggressive, and will spread rapidly, if not treated. The second factor is this: there is a form of treatment which, although not entirely satisfactory, offers at least some clear benefit to patients, by prolonging their eyesight for a span of months, or in some cases years.

This treatment is usually called "photodynamic therapy" (PDT). The drug that is most commonly used to carry out PDT is called verteporfin, sold under the trademark VISUDYNE by a joint venture between QLT Inc (www.qltinc.com) and Novartis Ophthalmics (www.novartis.com). Other drugs with similar activities and uses are being developed, including a drug referred to as SnET2 or rostaporfin, sold under the trademark PHOTREX by a company called Miravent. Accordingly, any references herein to verteporfin, or to laser-verteporfin treatment, are intended to be illustrative rather than limiting. It is believed and anticipated that the principles and teachings herein are likely to be equally applicable to PDT treatments using any specific type of PDT drug (including verteporfin, rostaporfin, etc., and any salts, analogs, and prodrugs thereof that may be used in PDT treatments), as can be evaluated by animal tests and/or human clinical trials using no more than routine testing.

Using verteporfin as an example, PDT treatment typically involves the following series of steps:

1. The drug is injected into the patient. It binds preferentially to low-density lipoproteins, which function as carriers, causing the verteporfin molecules to be transported preferentially to cells and tissues that are growing, including blood vessels that are actively growing behind the macula of a person with wet macular degeneration.

2. A period of time is allowed to pass, to ensure that the drug (bound to the LDL carrier molecules) has time to circulate through the patient, and into the growing capillaries in or behind his or her macula.

3. The patient is anesthetized, and a laser beam having a wavelength that will cause verteporfin to react is shone directly into the eye that is being treated.

4. When the laser beam hits the verteporfin molecules that are present in the thin-walled capillaries inside the retina, it causes a chemical reaction, which results in the verteporfin molecules breaking apart in a manner that causes them to release unstable and reactive molecules, usually called "oxygen free radicals" or "reactive oxygen species".

5. The unstable and highly reactive oxygen radicals that are released by laser-activated verteporfin, inside the growing macular capillaries, attack the interior walls of the capillaries. This damages them, and effectively seals them off.

6. The damage to the growing macular capillaries, caused by the radicals released by the verteporfin inside the capillaries that were hit by the laser, helps to inhibit any additional blood vessel growth in the retina, for some period of time.

Additional information on PDT drugs and methods is available in several review articles, including Algvere et al 2002 and Hunt et al 2003. Still more information is available on QLT's website, www.qltinc.com, which lists published clinical studies, and a historical account by the National Eye Institute is available at www.nei.nih.gov/neitrials/static/study60.htm.

It should be noted that PDT is distinct from a treatment called photocoagulation, which uses a very thin laser beam to effectively burn, cauterize, and seal off one blood vessel at a time.

The efficacy, extent, and number of months of relief that will be provided by PDT treatment in different patients varies substantially, depending on factors that are not fully understood but that are believed to include: (i) the extent of the damage and stress that have already occurred inside a patient's retina, and (ii) the extent of unwanted blood vessel growth that has already occurred inside that patient's retina.

Under the current state of knowledge and technology, PDT treatment is not ideal, and needs to be improved. As stated in Schmidt-Erfurth et al 2003, "the potential and success of the approach are considerably compromised". The known shortcomings of this treatment can be grouped into a number of categories, such as the following:

(1) Multiple treatments are required for most patients. For example, a recent review of a number of published articles describing clinical trials contained the statement, "Participants received on average five treatments over two years" (Wormald et al 2003). That number was merely an average, and many of those patients received larger numbers of treatments, in their struggle to keep their problem from getting worse.

(2) The results usually fall far short of being ideal, or restoring eyesight. When a series of multiple treatments is terminated, it is not because the patient has recovered, but because the physician and the patient both realize that still more treatments, costing multiple thousands of dollars each, will not provide any significant additional benefit.

(3) The net result of these treatments, in most patients, is that blood vessel growth and the resulting loss of eyesight is retarded for only a limited period of time, usually measured in months rather than years.

(4) When unwanted blood vessel growth begins to expand into an aggressive mode again, despite a series of PDT treatments, it usually signals that the end is approaching, and the patient will go functionally blind within a few months.

In addition to those "macroscopic" concerns that can be measured over patient populations, there are also concerns about the microscopic effects of verteporfin treatments, at the level of cells and molecules. Those factors include the following:

(a) Verteporfin blocks blood vessel growth by generating highly unstable, aggressive, and toxic "free radicals", which then begin attacking the cells inside the capillaries where the drug was located when it was hit and activated, by the laser. However, at least some of those toxic free radicals are carried out of those capillaries, by continuing blood flow, during the seconds and minutes before the full response kicks in, before those free radicals have time to react with the cells that line the insides of the retinal capillaries. This means that highly unstable and aggressively toxic molecules are being distributed, by continuing blood flow, throughout other structures and blood vessels in the retina and eye, during the seconds and minutes immediately after the verteporfin is activated by the laser beam.

(b) Despite the use of low-density lipoproteins as carriers that can "enrich" (to some extent) the concentrations of verteporfin in actively growing capillaries as compared to old and normal capillaries, that delivery system is only semi-selective, and does not reach or even approach a level that would be regarded as "highly selective". Low-density lipoproteins flow through every blood vessel and capillary; therefore, verteporfin-laser treatments cannot cleanly distinguish between unwanted capillaries that should be killed and sealed off, versus normal capillaries that are essential for providing nutrients to the retina and for removing waste metabolites from the retina.

(c) It has recently been reported (Schmidt-Erfurth et al 2003) that verteporfin-laser treatment stimulates, rather than suppresses, the release of hormones that increase blood vessel growth. Most notably, this includes a hormone called "vascular endothelial growth factor" (VEGF), discussed below. This hormonal response, which attempts to stimulate the growth of new blood vessels, is a normal and natural response in nearly any kind of tissue that must recover from a cut, bruise, broken bone, or other problem that disrupts blood supply.

The foregoing factors leads to two conclusions: (i) currently available PDT treatments are not ideal, or even close to ideal; and, (ii) their efficacy might be substantially improved, if methods or agents could be found for protecting desirable tissues, while focusing and targeting the damage more specifically toward the unwanted blood vessels.

For these reasons, a number of research efforts are underway, which are attempting to develop better methods for carrying out verteporfin-laser therapy. As one example, some ophthalmologists are studying the effects of injecting an anti-inflammatory steroid into a patient's bloodstream, as part of a PDT treatment. As another example, Spaide et al 2003 reported that if PDT treatment is followed immediately by an injection (directly into the vitreous humour, in the eye of a still-anesthetized patient) of an anti-inflammatory drug called triamcinolone acetonide (used today mainly for asthma and skin problems), the results of the PDT treatments appeared to be improved over the following months, when measured by periodic tests of visual acuity or retinal condition in treated patients.

In addition, methods are being tested for evaluating agents that can block certain specific types of growth hormones that are likely to be involved in abnormal blood vessel growth. One particular hormone that is receiving intense attention is called VEGF, which stands for "vascular endothelial growth factor". "Vascular" refers to blood vessels, and "endothelial" refers to the types of cells that make up the walls of blood vessels. Therefore, a growth factor that specifically stimulates the growth of "vascular endothelial" cells, which create blood vessel walls, clearly is a prime suspect in unwanted blood vessel growth, in patients with wet macular degeneration. Therefore, antibodies or other agents (including VEGF "aptamers") that can suppress the VEGF hormone (or that can occupy and block the cell-surface receptors that are activated by the VEGF hormone) are of great interest, among researchers and doctors studying ways of treating wet macular degeneration. Such agents are currently being tested in multi-center clinical trials, most of which are being sponsored by a company called Eyetech, which signed a licensing agreement with Pfizer in 2003. In various trials, anti-VEGF agents are being investigated by themselves, or in combination with verteporfin treatments. These trials are described in various articles such as Algvere et al 2002, and in a study authored by the Eyetech Study Group, published in *Ophthalmology* 110: 879-881 (May 2003).

Another hormone being studied closely is called pigment epithelium-derived factor (PEDF). Although this hormone normally helps suppress and control blood vessel growth, recent tests indicate that under certain conditions involving a protein called "mitogen-activated protein kinase" (MAPK), PEDF begins to act in combination with VEGF, so that both of them together have an even greater effect than VEGF alone, in stimulating blood vessel growth. These findings are discussed in Hutchings et al 2002, and in footnote 43 of Schmidt-Erfurth et al 2003.

It should also be noted that PDT treatments are occasionally used to treat certain types of eye problems that are not classified as wet (exudative) macular degeneration. For example, Wachtlin et al 2003 described the use of verteporfin to treat several types of problems that were grouped under the heading "inflammatory chorioretinal diseases". Those problems included punctate inner choroidopathy, presumed ocular histoplasmosis syndrome, multifocal choroiditis with panuveitis, and "other inflammatory conditions". The results indicated that verteporfin treatments for those conditions tended to perform better, and more effectively, than verteporfin treatments for wet macular degeneration. That result should not be surprising, since those types of inflammations tend to arise after a one-time infection, injury, or other insult that usually can be treated and resolved. By contrast, wet macular degeneration arises when the macula is suffering from some type of ongoing stress that causes the surrounding system to respond by trying to provide the area with additional blood supply.

Finally, it must also be noted that PDT treatments are very expensive. Internet postings state that each dose of verteporfin, used in a single treatment, costs more than $1000. That is the cost for that drug only, and it does not include any additional costs for physician or anesthesiologist services, clinic or hospital costs, or any other medication or service costs, all of which add up to multiple thousands of dollars per treatment.

Accordingly, despite progress in efforts to develop improved PDT treatments, there remains a critical need for ways to increase the safety and efficacy of such treatments.

Information On Zeaxanthin And Lutein

Because zeaxanthin is involved in this invention, background information needs to be provided on it, and on a related and similar compound called lutein. Both compounds are carotenoids, created naturally in plants and a few types of bacteria. Like other carotenoids, they cannot be synthesized by animals, and must be ingested as part of the diet.

The molecular structures of zeaxanthin and lutein (along with beta-carotene, for comparative purposes) are illustrated in FIG. 1. Like many other carotenoids, zeaxanthin and lutein are effective in absorbing ultraviolet light, and in neutralizing ("quenching") destructive compounds called radicals. Those are the primary functions of all carotenoids in plants, and in bacteria that must withstand direct sunlight for long periods of time.

However, unlike other carotenoids, zeaxanthin and lutein play special roles in the eyes of primates, including humans. They are the two carotenoid pigments that give the macula a yellowish tint; therefore, zeaxanthin and lutein are often referred to as the two "macular pigments".

The roles and activities of zeaxanthin and lutein, in human maculas, are described in articles such as Handelman et al 1988, Schalch 1992, and Snodderly et al 1995, and in U.S. Pat. No. 5,747,544 (Garnett et al 1998, which discloses a method of using zeaxanthin to treat or prevent macular degeneration) and Reissue patent Re-38,009 (Garnett et al 2003, which covers zeaxanthin formulations for human ingestion).

A number of factors can be used to point out similarities and differences between: (1) the roles and involvement of lutein and zeaxanthin in plants, where photosynthesis is crucial, and (2) their roles and involvement in animals, where photosynthesis does not occur and is irrelevant. Those factors can be gleaned from various disparate items of prior art; however, they have never been adequately correlated and analyzed in the manner provided below, and numerous skilled researchers and physicians who specialize in working with human health and eyesight apparently have failed to recognize or appreciate the existence, relationships, or significance of these factors. Therefore, these insights and correlations are not conceded to be prior art against this invention, and they are discussed in the Detailed Description section, below.

It should also be noted in particular that zeaxanthin and lutein are classified and regarded as anti-oxidants. This is highly important, because the literature published by QLT PhotoTherapeutics and Novartis Ophthalmics (which jointly sell verteporfin under the trademark VISUDYNE) contains a clear and explicit warning: "Compounds that quench active oxygen species or scavenge radicals, such as dimethyl sulfoxide, beta-carotene, ethanol, formate and mannitol, would be expected to decrease VISUDYNE activity."

Zeaxanthin and lutein fall squarely within that category; they are directly related to beta-carotene, and they clearly "quench active oxygen species or scavenge radicals".

Therefore, that published warning teaches directly away from the use of zeaxanthin to improve the results of verteporfin therapy. As an illustration of this principle, when the patient described below in Example 1 informed his ophthalmologist that he (the patient) was taking zeaxanthin, the ophthalmologist advised the patient, quite reasonably and in full accord with the warning that was published by the makers of verteporfin, that he (the patient) should stop taking zeaxanthin, since it might interfere with the treatment. However, the patient continued taking it anyway, against the advice of his doctor, and he received unexpectedly good results from the treatment, as described below.

Accordingly, one object of this invention is to disclose and provide a method of improving the results, efficacy, and benefits of photodynamic therapy using verteporfin or other drugs that create radicals or release toxins when activated by light, among patients with "wet" macular degeneration or other retinal problems.

Another object of this invention is to disclose and provide a non-invasive pre-treatment regimen, using orally-ingested zeaxanthin at a dosage and for a span of time that will result in a detectable increase in "macula pigment optical density" (MPOD), prior to photodynamic therapy, to increase the safety, efficacy, and benefits of the treatment.

Another object of this invention is to disclose that oral ingestion of at least 3, preferably at least 10, and even more preferably at least 20 mg/day of zeaxanthin, for a span of at least about a week and preferably 2 weeks or more, can improve the efficacy and benefits of photodynamic therapy, among patients with "wet" macular degeneration or similar retinal problems.

Another object of this invention is to disclose that orally-ingested zeaxanthin, taken as a "pre-loading" step prior to a PDT treatment, can improve the efficacy and benefits of the PDT treatment.

These and other objects of the invention will become more apparent through the following summary, drawings, and detailed description.

SUMMARY OF THE INVENTION

Zeaxanthin pre-treatment can improve the benefits and efficacy of photodynamic therapy (PDT), which uses a drug such as verteporfin in patients who suffer from unwanted retinal blood vessel growth (including the "wet" (exudative) form of macular degeneration). Before a PDT treatment, patients are given a regimen of orally-ingested zeaxanthin, for a period such as at least 1 and preferably at least 2 to 3 weeks, at dosages of at least 3, preferably at least 10, and more preferably 20 or more milligrams per day. Since zeaxanthin imparts a yellowish color to the macula, effective dosage levels for any individual can be determined and adjusted by using non-invasive measurements of "macular pigment optical density" (MPOD). The zeaxanthin dosage preferably should increase a patient's macular pigment density before the PDT treatment is performed.

Alternately or additionally, preferred dosages for one or more classes of patients can be determined by the outcome(s) of one or more human clinical trials, as described below. Similarly, if a patient is suffering from a condition that indicates immediate and drastic treatment should be performed, to try to save as much eyesight as possible by immediately treating a rapid deterioration in eyesight or eye health, intravenous injection or infusion of zeaxanthin, to boost levels in circulating blood as quickly as possible, can be carried out.

This type of treatment regimen is referred to herein as "pre-loading", since the goal of the treatment is to have zeaxanthin already deposited (or "loaded") into the retinal cells and tissues, by the time a PDT treatment session is carried out. If desired, zeaxanthin administration can be terminated or reduced a few days before a PDT treatment is performed, to reduce zeaxanthin concentrations in circulating blood (as distinct from zeaxanthin that has already been deposited into cells).

Because of certain molecular and cellular factors, it is anticipated that the 3R,3'R stereoisomer of zeaxanthin (which occurs naturally, in the diet) will perform in a manner that is superior to, and safer than, either of two other macular pigments, which are: (i) lutein, a structural isomer of zeaxanthin that has a lower level of "conjugation" and a smaller "electron cloud" that plays a crucial role in absorbing ultraviolet and near-UV light and destructive free radicals; and, (ii) meso-zeaxanthin, a non-dietary stereoisomer of zeaxanthin that has a "sinister" or "levorotatory" arrangement at one end that has never been found in any dietary sources. Although 3R,3'R-zeaxanthin is preferred for use as disclosed herein, preloading treatments that administer lutein or meso-zeaxanthin to a patient prior to PDT are also covered by some of the claims, for reasons described below.

BRIEF DESCRIPTION OF THE DRAWINGS

FIG. 2 depicts a number of biochemical pathways that are believed to be involved or activated in various tissues, when photodynamic therapy is performed. A number of these pathways cause or aggravate various adverse and unwanted side effects, such as stimulated production and/or release of vascular endothelial growth factor (VEGF), which can aggravate the formation of new blood vessels, after a PDT session has occurred.

FIG. 3 depicts the same set of pathways as FIG. 2, and also indicates a number of candidate mechanisms that may help explain the benefits of zeaxanthin pre-loading, before a PDT session. These mechanisms use a small schematic depiction of zeaxanthin, to indicate unwanted metabolic pathways that may be suppressed or minimized by zeaxanthin.

DETAILED DESCRIPTION

Figure 1:
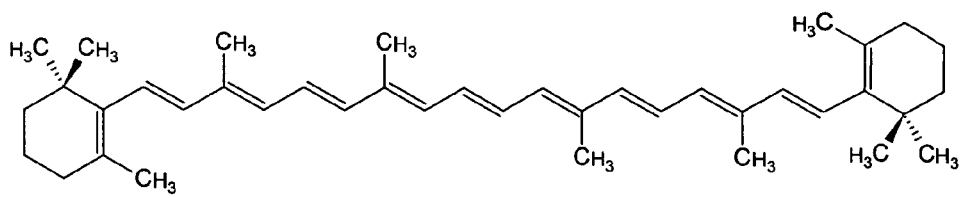
FIG. 1 shows the chemical structure of 3R,3'R-zeaxanthin, along with beta-carotene, meso-zeaxanthin, and lutein for comparative purposes. Although the alternating single and double bonds are shown in fixed positions in these drawings, the electrons are actually in a "resonant" structure (or cloud) that is distributed across the entire straight-chain portions of these molecules. This movable electron cloud allows carotenoids to absorb and "quench" ultraviolet photons and destructive radicals, without damaging the carotenoids. R,R-zeaxanthin is fully symmetric, with "beta" rings at both ends, while lutein is not symmetric, and has an "epsilon" ring at one end. Zeaxanthin has a higher degree of conjugation, and a longer and larger electron cloud that covers a portion of both of its beta rings. This allows it to provide better protection against UV photons and destructive radicals than lutein, which has no electron cloud over its epsilon ring.
Figure 1:
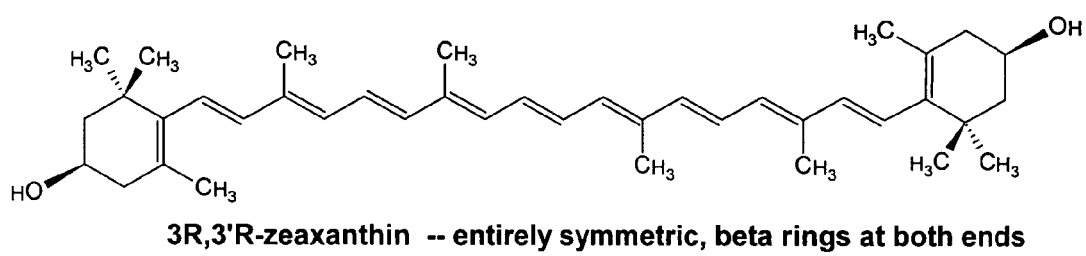
Figure 1:
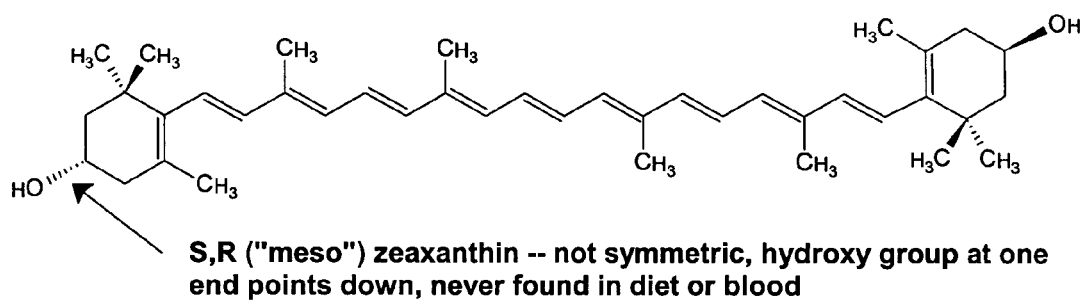
Figure 1:
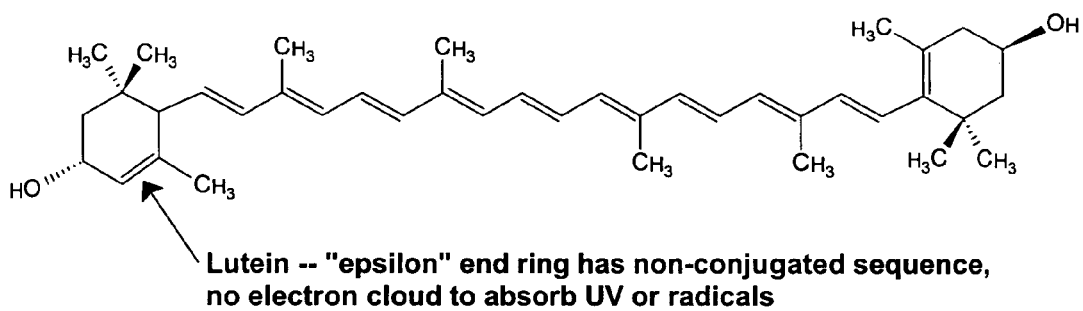

As summarized above, pretreatment of a patient with a regimen of orally-ingested zeaxanthin, prior to a PDT treatment for wet macular degeneration or a chorioretinal problem involving unwanted blood vessel growth, can improve the benefits and efficacy of the PDT treatment. The zeaxanthin "pre-loading" preferably should involve dosages of at least 3 milligrams per day (preferably at least 10 mg/day, and even more preferably 20 mg/day or even higher, up to about 100 mg/day per day), for a period of at least about 1 week and preferably at least 2 to 3 weeks.

Since zeaxanthin imparts a yellowish color to the macula, effective and preferred dosage levels for any individual patient can be determined and adjusted, by using non-invasive measurements of "macular pigment optical density" (MPOD), and by comparing MPOD levels before and after the zeaxanthin treatment begins. Alternately or additionally, preferred dosages for one or more classes of patients can be determined by the outcome(s) of one or more human clinical trials, as described below.

Since zeaxanthin is a natural macular pigment, and since it apparently functions in the manner of a vitamin, which can help protect the macula against UV and near-UV radiation and oxidative damage, a regimen of oral zeaxanthin preferably should be commenced promptly, by any patient who is experiencing macular or other eye or vision problems, regardless of whether that patient is planning or likely to receive PDT therapy. Therefore, there is no upper limit to the time period that should be used to "pre-load" a patient who will receive PDT therapy.

However, if desired, any patient who has been taking zeaxanthin for at least two weeks or more can temporarily stop taking the zeaxanthin for a brief period (such as 3 to 7 days) prior to a PDT treatment session. This may slightly reduce the concentrations of zeaxanthin that are suspended in circulating blood, during and immediately after a PDT therapy session, without reducing the quantities of zeaxanthin that have been deposited in a protective manner into the surrounding cells and tissues.

In mid or late 2003, based on various ongoing reviews of the scientific and medical literature concerning zeaxanthin, and because he had studied the drugs and mechanisms involved in photodynamic therapy for patients with wet macular degeneration, the Applicant herein began to suspect that pretreatment with zeaxanthin might be able to help improve the outcomes and net benefits, in at least some patients, that can be provided by PDT therapy. Some of the pathways and mechanisms that were believed to be involved are described below and illustrated in FIGS. 2 and 3.

In order to evaluate that hypothesis, the Applicant began looking for either an existing or candidate customer who was taking zeaxanthin because of a macular degeneration problem, and who was planning to have PDT treatment for his or her condition.

Such a candidate became known to the Applicant, in mid to late 2003. Because of certain personal and business connections, he was contacted by a man in his late 70's, who had been told that (i) his eyesight was deteriorating rapidly, due to macular degeneration, and (ii) he should take care of any business, financial, legal, and other matters as soon as possible, before his eyesight became even worse. This person made his plight (and his severe depression, due to the very negative prognosis he had received from an expert) known to the Applicant. In response, the Applicant informed the patient that he (the Applicant) had made a number of charitable donations to support research at the Johns Hopkins School of Medicine, where some of the world's foremost experts in macular degeneration work. He (the Applicant) offered to see whether he could obtain expedited treatment for the patient, by making some phone calls to people he knew who worked there. The patient accepted that offer, and was seen and treated not long thereafter, by a top expert at the Wilmer Eye Institute, a highly respected eye care and research institute affiliated with Johns Hopkins.

This patient had been taking zeaxanthin for a number of weeks, prior to being examined and treated at the Wilmer Eye Institute. His dosage was believed to be 20 milligrams per day, from taking two 10 milligram capsules (purchased from ZeaVision LLC) per day, usually with meals. He also took various other vitamin supplements during the course of his treatment, and afterwards.

When the patient told the ophthalmologist that he was taking zeaxanthin supplements, the ophthalmologist suggested that the patient should stop, because zeaxanthin might interfere with the treatment. That advice was in accord with a published warning that accompanies all advertising and sales of verteporfin, which states, "Compounds that quench active oxygen species or scavenge radicals, such as dimethyl sulfoxide, beta-carotene, ethanol, formate and mannitol, would be expected to decrease VISUDYNE activity." Despite that advice from the ophthalmologist, the patient continued taking zeaxanthin, up until (and after) his treatment.

The ophthalmologist recommended that the patient should begin taking the AREDS combination of beta-carotene, vitamins C and E, and zinc. It is not known to the Applicant whether that advice referred to a regimen that was being recommended for after the PDT treatment had been completed.

The ophthalmologist also advised the patient that his course of treatment likely would require 5 or 6 verteporfin-laser treatments, over a span of up to about 2 years.

The first verteporfin-laser treatment was carried out in the normal manner, in July 2003. When the patient was examined again three months later, the ophthalmologist was surprised by how well the results had turned out. He informed the patient that the results were far better than expected, and that instead of needing 5 or 6 treatments over the next 2 years, the patient likely would need only 1 or 2 treatments.

That result, described in more detail in Example 1, below, has been supplemented and supported by additional information, summarized in Example 2, arising from a survey that was carried out by the assignee company (ZeaVision LLC) of customers who: (i) are buying and consuming zeaxanthin supplements from ZeaVision, and (ii) suffer from the wet form of macular degeneration, and have had at least one PDT therapy session.

While that survey falls short of the rigorous standards of a double-blinded multi-site clinical trial, the results nevertheless are positive, and clearly suggest and indicate that: (1) zeaxanthin apparently did not interfere with the efficacy of PDT treatment, and did not cause any adverse side effects of any sort in any patients who were surveyed; and, (2) in at least some patients, zeaxanthin apparently provided at least some benefits, and therefore apparently was worthwhile and advisable.

The Applicant herein has been studying the literature in this field of research for years, and has identified a number of articles that set forth mechanisms and rationales that may help explain how zeaxanthin can help improve the outcomes of PDT treatment using drugs such as verteporfin. While this invention is not tied or limited to any particular theory of how or why it functions in the way it does, several potential contributing factors are listed below, or are illustrated in FIGS. 2 and 3. This description and illustration of apparent and potential contributing factors is intended: (i) to help researchers and ophthalmologists develop a better understanding and theoretical foundation for why this method works as it does; (ii) to help convince agencies, companies, and ophthalmologists that this method deserves high-priority evaluation; and, (iii) to help researchers in this field create and plan tests and experiments that may be able to help quantify the extent to which any such factor may be contributing to the benefits of this treatment, in one or more categories of patients.

Accordingly, these hypotheses and citations are offered as suggestions and guideposts, for anyone who wishes to begin looking in greater detail into these types of potentially contributing factors:

(1) Any zeaxanthin that has been deposited in cells and cell membranes, in tissues in and around the retina (as distinct from remaining in circulating blood), may be able to help quench and extinguish undesirable free radical reactions that could otherwise (i) damage retinal cells and tissue directly, or (ii) trigger the release of stress hormones or other signaling factors that might otherwise promote the recruitment and/or growth of more blood vessels or lead to other undesired effects. This factor can be better understood in light of articles such as Beatty et al 2000, and in light of FIGS. 2 and 3.

(2) Since lipoperoxides have been shown to stimulate the growth of retinal blood vessels in animal models (e.g., Tamai et al 2002), zeaxanthin's ability to help quench the formation and/or propagation of lipoperoxides (including a process referred to as "photosensitized" peroxidation of lipids, as described in Wrona et al 2004) suggests additional modes of action that may benefit patients suffering from retinal neovascularization, especially if zeaxanthin is also combined with other antioxidants (e.g., Wrona et al 2003 and 2004).

(3) Since oxidative stress can adversely affect "gap junction" communications and other activities of RPE cells (e.g., Bailey et al 2004), zeaxanthin's ability to reduce that type of oxidative stress suggests yet another potential mode of action.

(4) Studies on similar xanthin carotenoids, such as astaxanthin, have shown that they can help reduce inflammatory and similar responses triggered by oxidative and/or chemotactic signals, such as involving inflammatory cytokines (e.g., Ohgami et al 2003, Lee et al 2003). Xanthin carotenoids (also spelled as xanthine carotenoids, and also referred to as xanthophyll carotenoids) are defined as carotenoid compounds that contain at least one oxygen atom, and include zeaxanthin, lutein, astaxanthin, canthaxanthin, etc. Since zeaxanthin is structurally similar to such other xanthin carotenoids, and since zeaxanthin is specifically deposited into the human macula, there are reasons for presuming that zeaxanthin can perform the same roles more effectively than astaxanthin, in the human macula.

(5) A recently published abstract (Fernandez et al 2004) suggests that a combination of lutein (which also contains some quantity of zeaxanthin, in all commercially available lutein preparations) and glutathione can reduce the expression and activity of both "vascular endothelial growth factor" (VEGF, discussed in the Background section) and metalloproteinase enzymes (such as MMP-2), which tend to aggravate choroidal neovascularization.

(6) In addition, a number of articles and books on the roles and benefits of carotenoids in skin have been published, and describe various pathways and mechanisms that enable carotenoids to help protect skin. A major recent book, Krinsky et al 2004, contains a highly useful chapter on this subject, while recent review articles include Stahl et al 2002 and 2003.

FIG. 2 offers a schematic depiction of various cellular, physiological, and biochemical pathways that are believed likely to be involved, at varying levels, in patients who are receiving PDT treatments. Near the top of the drawing, the primary mechanism of PDT is shown by a progression from left to right, in which laser activation of verteporfin or a similar drug will generate reactive oxygen species, which are highly aggressive, and which will attack the interiors of growing thin-walled blood vessels that (i) contain the drug, and (ii) are hit by a laser beam having an activation wavelength.

That is the primary therapeutic mechanism, but it is surrounded and complicated by a number of additional pathways, including the following:

(1) Other types of etiologies will also be generating non-specific, untargeted, generally unhelpful oxygen radicals;

(2) The creation of hypoxic and/or ischemic stress, due to the PDT treatment and possibly other factors, can also lead to the generation of more oxygen radicals, and to the creation and/or aggravation of additional problems, such as (i) increased expression and/or release of vascular endothelial growth factor (VEGF), (ii) increased expression and/or release of various inflammatory cytokine hormones, and (iii) recruitment of certain types of monocyte cells, into retinal and/or surrounding tissues;

(3) The creation of oxygen radicals by the PDT treatment or other factors can also stimulate the formation of lipoperoxides, which are unstable and reactive compounds formed mainly from the lipid constituents of cell membranes. These lipo-peroxides (and oxygen radicals released by them) can lead to increased expression and/or release of additional factors, including "tumor necrosis factor (TNF), alpha-1 interleukin, transforming growth factors (T-GF), and/or pigment-derived growth factors (PDGF), all of which can further increase and aggravate the expression and/or release of VEGF.

(4) The expression and/or release of VEGF leads to additional problems, including angiogenesis (i.e., the direct formation of new blood vessels, which is not what someone wants if being treated to suppress the growth of new blood vessels), and release of certain metalloproteinase enzymes, which also can cause problems.

(5) The processes of inflammatory cytokine hormone release and monocyte cell recruitment can also damage the Bruch's membrane layer, leading to still more problems, and to the release and emission of still more distress signals that will lead to more blood vessel growth.

FIG. 3 depicts a number of ways in which zeaxanthin may be able to help control and minimize some or all of those contributing factors. The most likely anticipated and hypothesized mechanisms of protection, for at least some patients, are indicated by the stylized schematic drawing of zeaxanthin, placed across an arrow that represents an unwanted and unhelpful pathway.

Accordingly, those skilled in the art who are interested in knowing more about how zeaxanthin may help benefit PDT treatments should review the above-cited articles and FIGS. 2 and 3, and consider what those items suggest about candidate modes of action that may help explain the benefits of zeaxanthin pre-loading prior to PDT treatment.

The results summarized above, the literature cited above, and additional information that has become known to the Applicant during more than 10 years of working with zeaxanthin, have all combined to convince the Applicant of the following:

(i) the likelihood is very high that, for a number of cellular and physiological reasons, pretreatment with zeaxanthin can provide a useful and beneficial form of protection to the retinal area, which can render several types and layers of retinal tissue more capable of withstanding any ischemic and other insults within the macula or retina that are created by light-activated drugs that release radicals and/or toxins, and can minimize any lingering or permanent damage to those cells and tissues;

(ii) ophthalmologists who perform PDT therapy should begin testing zeaxanthin pre-loading, as part of their overall course of treatment, to determine whether such pre-loading will provide substantial benefits to all patients, or to specific categories of patients who are treated with one or more types of PDT drugs; and, (iii) because definitive studies have not yet proven whether zeaxanthin is indeed more effective than lutein at protecting the macula in these types of treatments, clinical trials involving zeaxanthin pretreatments preferably should test at least three different treatment arms against a control group, preferably in a double-blinded study. In the recommendation of the Applicant, those three treatment arms should include:

(a) pretreatment using orally-ingested zeaxanthin alone, without lutein, preferably at a dosage of at least 3 and preferably at least 10 or 20 mg/day, for a period of at least 2 weeks and preferably at least a month;

(b) pretreatment using oral lutein alone, without any additional zeaxanthin (beyond the small quantity of zeaxanthin that is already contained in commercially-available lutein supplements), at a daily dosage identical to the dosage of the zeaxanthin-only tests; and, (c) pretreatment using both oral zeaxanthin and oral lutein, at the same dosage selected for the tests above, divided equally (50-50) between zeaxanthin and lutein.

For reasons described below, the Applicant believes and anticipates that the zeaxanthin-only treatment group will fare the best, compared to the untreated control arm. However, at this time, that is only a hypothesis, and the Applicant fully expects and agrees that the data from a properly planned and controlled test should determine both: (i) the outcome of any such trial, and (ii) the final recommendations for preferred treatment dosages, for zeaxanthin and/or lutein.

These positions and assertions can be better understood in light of the following comments and observations.

Comparisons Between Zeaxanthin and Lutein

In evaluating the ability of zeaxanthin and lutein to help maximize the benefits and minimize the unwanted side effects of PDT therapy, the factors listed below should be taken into account. As mentioned in the Background section, these factors can be located in various different sources. However, these factors have never previously been compiled and correlated in this manner, and they apparently are not adequately recognized, understood, or appreciated by those skilled in vision research or ophthalmology.

The relevant factors include the following:

(1) Lutein is bent (or "kinked") at the end that contains the "epsilon" ring. This bend, near one end of the molecule, enables lutein to fit into circular "light-harvesting structures" in chloroplasts, which are organelles in plant cells that play major roles in photosynthesis.

(2) Since zeaxanthin has "beta" rings at both ends, it is straight, with no bend or kink. Therefore, it cannot fit properly into the circular light-harvesting structures that are crucial for photosynthesis, in plants. Even in plants where zeaxanthin does occur, it does not accumulate in substantial quantities; instead, it becomes part of a daytime/nighttime cycle, which shuttles the molecule back and forth between zeaxanthin and a different carotenoid called violaxanthin.

(3) Because of its role in light harvesting structures, lutein became a heavily dominant carotenoid in plants, while zeaxanthin is present only in very small trace amounts. Even in dark green plants with high concentrations of zeaxanthin (such as spinach or kale), concentrations of lutein are dozens or hundreds of times greater than zeaxanthin.

(4) Although lutein is dominant in plants, which must be able to harvest light and carry out photosynthesis, animals do not carry out photosynthesis. Animal cells do not have, use, or need chloroplasts, or light-harvesting structures. Therefore, the advantages of lutein, a bent-chain molecule that fits ideally into circular light-harvesting structures in plants, become totally irrelevant, in animals and animal cells. After ingestion by an animal, the advantages of zeaxanthin, over lutein, move to the forefront.

(5) Zeaxanthin has a higher level of conjugation than lutein. This term refers to the fact that when bonds between adjacent carbon atoms alternate between single bonds and double bonds, in a regular and repeating manner, the electrons that form those bond take on a "shared" arrangement, and create what is often referred to as an "electron cloud". This same result also occurs in benzene rings and other "aromatic" molecules, discussed in any textbook on organic chemistry.

(6) As can be seen from the molecular structures of zeaxanthin and lutein, in FIG. 1, the straight chain portion of both molecules is fully conjugated, and surrounded by an electron cloud. This is conventional for many and even most carotenoids, and the differences between them arise in their end rings.

(7) In zeaxanthin, the conjugated "electron cloud" covers parts of both of its two end rings, since the alternating sequence of single and double bonds extends into both of zeaxanthin's end rings. By contrast, in lutein, the "epsilon" end ring does not contain or extend an alternating sequence of single and double bonds. Therefore, the conjugated electron cloud of lutein covers a portion of only one of the end rings, in lutein; it does not cover any part of the "epsilon" end ring of lutein.

(8) A conjugated "electron cloud" is absolutely crucial to the two protective activities that caused carotenoids to become widespread in the plant world. First, a surrounding electron cloud enables carotenoids to absorb ultraviolet and near-UV radiation, without being badly damaged and broken apart. Second, a surrounding electron cloud also enables carotenoids to absorb oxygen radicals, which contain aggressive and unstable unpaired electrons. Carotenoids evolved and became widespread, in the plant world, because their conjugated bonds and electron clouds render them ideally suited to deal with both of those threats to cells and tissues. They were then adapted and utilized by animals to serve the same protective roles, even though animals cannot synthesize them and must eat them in their diets.

(9) Because of the hydroxy groups attached to their end rings, zeaxanthin and lutein are deposited in ways that cause them to "span" or "straddle" the outer membranes of animal cells. This places zeaxanthin or lutein in a direction that is perpendicular to a cell surface, with a portion of each end ring protruding from both the interior and exterior surfaces of the cell membrane.

It should be noted that beta-carotene has a totally different type of membrane deposition, and an entirely different fate. Since it is made entirely of hydrogen and carbon, with no oxygen atoms or hydroxy groups, it is deposited in cell membranes in a way that aligns it entirely within the oily center layer of a cell membrane. Unlike zeaxanthin or lutein, its main fate is to be broken in half, to release retinol (Vitamin A).

Incidentally, it is not a mere coincidence that the "xanthin" carotenoids such as zeaxanthin, lutein, castaxanthin, and astaxanthin (which are formed by adding oxygen atoms or hydroxy groups to beta-carotene) have lengths that allow them to extend slightly beyond the thickness of an animal cell membrane. Carotenoids and animal cell membranes co-evolved over the eons, in ways that created a "partnership" that allows them to interact with each other.

(10) When it has been deposited into an animal cell membrane, zeaxanthin's straight-chain structure is ideal, since it allows zeaxanthin to fully extend portions of both of its two end rings (with their protective electron clouds) slightly beyond both of the inner and outer surfaces of an animal cell membrane. By contrast, the bent and kinked structure of lutein hinders and impedes its ability to properly span an animal cell membrane. Indeed, some in vitro tests using liposomes have suggested that part of the lutein in an animal system doesn't even straddle cell membranes at all, and instead remains within a membrane interior, in a manner similar to beta-carotene.

(11) Even when lutein molecules do straddle an animal cell membrane, they can provide a conjugated and protective (UV-absorbing, radical-quenching) electron cloud on only one side of that membrane, where the "beta" ring is located. As mentioned above, the epsilon ring at the other end of a lutein molecule has no protective conjugated cloud at all.

As a result of these factors (and possibly others), it is believed by the Applicant that zeaxanthin can perform, in humans, in ways that can provide greater benefits than lutein, especially in eye tissues.

This belief is supported by two known factors. First, it is known that the retina deposits zeaxanthin preferentially over lutein. Zeaxanthin is deposited at the highest concentrations directly into the crucial center of the macula, while lutein is deposited at higher concentrations around the edges and periphery of the macula. While the mechanisms that enable this to occur are not fully understood, it recently has been reported that certain enzymes that appear to be involved will clearly bind to zeaxanthin with relatively high affinity, under in vitro conditions, but those same enzymes will not bind to lutein with any significant affinity. This is a potentially very important finding, described in Bhosale et al 2004.

Second, it is also known that the macula attempts to convert lutein into zeaxanthin. However, that conversion process cannot convert lutein into the normal stereoisomer of zeaxanthin that is found in nature (the 3R,3'R stereoisomer); instead, it converts lutein instead into a different stereoisomer that has never been found in any food sources or mammalian blood. That non-dietary isomer has one end ring with the conventional "R" configuration, but the second end ring has an unnatural "S" configuration that is not found in any dietary sources. That S-R isomer is often called meso-zeaxanthin.

Except for very small amounts that can be found in human retinas as a result of the lutein conversion process, meso-zeaxanthin has never been found in nature, or in any plant or food sources. This assertion requires an explanation and defense, since it contradicts a claim that was published in 1986, by researchers who were working in Japan. Maoka et al 1986 asserted that meso-zeaxanthin had been found in certain types of marine life, such as in the skins of certain types of fish. However, that claim was directly contradicted, years later, by Khachik et al 2002, which showed that the type of alkaline processing that was used by Maoka et al, actually caused lutein to be converted into meso-zeaxanthin, because of a chemical process that apparently was first described in Bone et al 1993. In other words, the chemical processing used by Maoka et al to extract and treat their carotenoid samples, actually created meso-zeaxanthin, as a misleading artifact that was created and caused by their chemical processing steps.

The chemical conversion that causes lutein to be converted into meso-zeaxanthin, when treated with a strong alkali, was first described in Bone et al 1993, which was years after Maoka et al published their article in 1986. Therefore, the mistake by Maoka et al was innocent. However, anyone interested in the 1986 assertion that meso-zeaxanthin was found in marine life, as reported in 1986, should study page 3388 of Khachik et al 2002, which reported that:

(1) When the same processing steps that had been used by Maoka et al were followed by Khachik et al, meso-zeaxanthin appeared to be present in human blood;

(2) However, when more recent and accurate processing methods were used by Khachik et al, meso-zeaxanthin was shown to be not present, at all, in human blood.

In other words, Khachik et al 2002 directly refutes and contradicts the claim made in Maoka et al 1986, by showing that the chemical processing steps used by Maoka et al in the 1980's could and would create meso-zeaxanthin, as a misleading artifact, when carried out on a biological fluid sample.

Since meso-zeaxanthin has never been found in human blood, there is a consensus that the meso-zeaxanthin found in human maculas must be formed by a lutein conversion process. Accordingly, the fact that the human macula does indeed try to convert lutein into zeaxanthin (resulting in a stereoisomer that does not otherwise exist in nature) is strong evidence that the human eye "prefers" zeaxanthin over lutein.

For the reasons summarized above, zeaxanthin is believed to offer better protection, for human retinas, than lutein. However, this belief needs to be evaluated and confirmed, by studying data generated by clinical trials. The trials described herein can provide a direct comparison between zeaxanthin and lutein, using PDT treatments in conjunction with three different pre-loading treatments: (i) orally-ingested zeaxanthin only; (ii) lutein and zeaxanthin, in a 50-50 ratio; and (iii) lutein preparations only (however, noting that all commercial lutein preparations also contain some zeaxanthin, usually about 1 to 5% by weight).

Three additional points should be noted. First, it is believed that treatment with zeaxanthin is believed to be entirely free of any significant risks, among people who are suffering from macular degeneration or other eye problems. That statement is supported by a "New Dietary Ingredient" application that was filed on zeaxanthin, with the U.S. Food and Drug Administration, by Roche Vitamins, Inc. That NDI application contained extensive safety data, including data from animal tests indicating that even at very high dosages, zeaxanthin did not cause any pathological changes, of any sort, in animal tests. The docket number of that NDI application, published in June 2001, is 95S-0316. It can be downloaded at no charge from the FDA website. Accordingly, it is believed that clinical trials as proposed herein can be carried out without any significant risks to any patients.

Second, this is a very low-cost treatment, compared to the costs of a verteporfin-laser treatment. Each drug and laser treatment costs thousands of dollars each. By contrast, 60 capsules of zeaxanthin, containing 10 mg each, cost roughly $60, from www.zeavision.com.

Third, such treatments, in addition to focusing on patients who suffer from wet macular degeneration, may also (if desired) include and focus on PDT treatments for patients who suffer from other chorioretinal problems, such as punctate inner choroidopathy, presumed ocular histoplasmosis syndrome, or multifocal choroiditis with panuveitis, as described in Wachtlin et al 2003).

Zeaxanthin Isomers And Esters

Because of its close similarities to the natural dietary 3R,3'R stereoisomer of zeaxanthin, the non-dietary S,R isomer called meso-zeaxanthin may be able to generate similar protective benefits, if used as an macular pigment agent prior to a PDT treatment as disclosed herein. Accordingly, any references herein to "zeaxanthin" are intended to include the "meso" isomer of zeaxanthin, and the claims below are specifically intended to cover and include meso-zeaxanthin, as one form of zeaxanthin.

However, any suppliers or ophthalmologists who might wish to consider selling or using meso-zeaxanthin as a pretreatment agent for improving the outcomes of PDT therapy should be aware of several concerns and questions that should be evaluated carefully, before any such efforts commence. Those questions and concerns include:

(i) as summarized above, Khachik et al 2002 contradicts the claim in Maoka et al 1986 that meso-zeaxanthin was found in certain types of marine life;

(ii) if meso-zeaxanthin is indeed a non-dietary isomer, as stated in a number of published articles, and if it is being manufactured by chemical treatment of lutein, then the statutory language in the Dietary Supplement Health and Education Act (the DSHEA statute, passed by Congress in 1994) would appear to require certain legal requirements to be met before it can be sold or administered to humans. In particular, the language concerning "chemically altered" food compounds, in section 413 of the DSHEA act (codified in 21 U.S. Code 350b) needs to be evaluated carefully; and, (iii) when a test was done in Spain to compare a meso-zeaxanthin preparation against a zeaxanthin preparation containing the dietary 3R,3'R stereoisomer, as a color additive for poultry, the meso-zeaxanthin preparation did not perform satisfactorily, as described in Perez-Vendrell et al 2001. Based on a website posting that apparently is no longer available, supplemented by inquiries by an industry consultant, it is believed by the Applicant that a similar test was done in Mexico, which also showed unsatisfactory poultry pigmenting results for meso-zeaxanthin; however, those results apparently were never published. Those results raise important questions about the deposition of meso-zeaxanthin, in animal tissues.

Accordingly, the natural and dietary 3R,3'R isomer of zeaxanthin is strongly preferred for use herein, over the meso isomer of zeaxanthin. However, certain companies (mainly suppliers located outside the United States, who are not directly affected by the DSHEA law that applies in the United States) have begun advertising "zeaxanthin" that was created by chemically isomerizing lutein, apparently without warning prospective purchasers that the "zeaxanthin" they are offering is actually a non-dietary isomer. Accordingly, since an issued patent allows the owner to prevent others from making, using, or selling a patented invention without lawful permission, all references to "zeaxanthin" in the claims herein are specifically intended to also include the meso-zeaxanthin isomer. This does not state or imply that R,R-zeaxanthin (as found in fruits and vegetables) and S,R meso-zeaxanthin (the nondietary stereoisomer) are equivalent; they are not, and the distinction between them should be understood and made clear and explicit, in any labeling or advertising. Nevertheless, because of the reasons set forth above, both of those two different stereoisomers of zeaxanthin are included within the term "zeaxanthin" as used in the claims.

In addition, any references herein to "zeaxanthin" include esters of zeaxanthin. Most plants and many bacteria synthesize lutein and zeaxanthin, not in the form of "free" carotenoids (also called "alcohol" carotenoids), but with one or two fatty acids linked to the hydroxy groups in a manner that creates an ester bond. However, when these esters are ingested by animals, most of the ester linkages will be broken, in a manner that releases free (non-esterified) zeaxanthin or lutein. This chemical reaction is called "hydrolysis", since a water molecule is effectively inserted into what was previously the ester bond. These reactions are catalyzed by "esterase" enzymes, and by various other digestive enzymes. Accordingly, since zeaxanthin or lutein esters will release free zeaxanthin or lutein, after ingestion by an animal, they are regarded as nutritionally equivalent, and any reference herein to any xanthin carotenoid also includes the ester form.

Optional Additional Agents

If zeaxanthin is used in the manner described herein, it can be combined with any additional agent(s) that may also be able to provide one or more additional benefits. For example, Vitamins C and E, and zinc, can be administered, although any such zinc dosages preferably should be reduced to dosages lower than were tested in the AREDS trial, because of certain concerns involving potential neurological risks in elderly consumers (including beta-amyloid plaque formation and growth, as described in various papers by Ashley Bush and others, and potential aggravation of brain damage is a stroke or similar crisis occurs, as described in various papers by Dennis Choi and others), which apparently have not been cited in any of the reports to date that describe the outcomes of the AREDS trial. Similarly, lutein can also be administered, although it is not preferred for use herein, for reasons described in the Background section.

Astaxanthin also is a candidate agent that should be evaluated for such use, both with and without zeaxanthin. Because it has a chemical structure that resembles zeaxanthin in several respects (with a conjugated electron cloud that covers part of both of its two end rings in a manner comparable to zeaxanthin), and because it has already been approved for human use as a food additive, astaxanthin may provide a relatively potent and effective candidate agent for such use, and may even be able to substitute for zeaxanthin in some formulations. As mentioned in the Background section, reports such as Ohgami et al 2003 and Lee et al 2003 have indicated that astaxanthin can help reduce inflammatory and similar responses triggered by oxidative and/or chemotactic signals such as inflammatory cytokines. Therefore, astaxanthin is regarded as a highly promising candidate agent, for use either with or without zeaxanthin, to increase the benefits and inhibit any unwanted adverse effects of photodynamic therapy. Accordingly, one embodiment of this invention can be described as administering a xanthin carotenoid to a patient in need of photodynamic therapy, at a dosage and for a duration sufficient to cause deposition of the xanthin carotenoid in at least one type of ocular tissue prior to performing photodynamic therapy.

On that subject, it should be noted that when canthaxanthin was orally ingested at very heavy dosages, for a period of multiple months in succession, by people who wanted deep and dark suntans, it led to a form of abnormal retinal deposition, described as resembling "tiny bits of gold dust" in the retina. While this indicates that xanthin carotenoids other than just lutein and zeaxanthin can be deposited into retinal tissue, it should also serve as a cautionary warning that any use of a xanthin carotenoid other than the two natural macular pigments (zeaxanthin and lutein) should be carefully monitored to ensure that it does not create an aberrant form of retinal deposition, at the dosages and durations used.

The risk of pathology being caused by a carotenoid such as canthaxanthin will depend heavily on the dosages that are ingested, if it is taken as a supplement. However, the history of retinal pathology caused by canthaxanthin suggests that it does not offer a preferred candidate, and it almost certainly will not be used by reputable ophthalmologists, in view of its history of retinal pathology. Nevertheless, high-dosage canthaxanthin is being advertised and sold to the public over the Internet, under conditions that raise serious questions about the legality of such sales and use. Therefore, to reduce the risks of illegal sale or abuse, canthaxanthin is included within the term "xanthin carotenoid" as used in various claims.

In addition, a number of additional candidate agents are listed in U.S. application Ser. No. 10/746,403, filed in December 2003 and scheduled to be published soon on the U.S. Patent Office website (the contents and teachings of that application are incorporated herein by reference, as though fully set forth herein). Such agents, which are known to provide various ocular benefits in at least some categories of patients, include docosahexaenoic acid (DHA, an essential fatty acid), alpha-lipoic acid, taurine, carnosine, carnitine, Coenzyme Q10, glutathione-boosting compounds such as N-acetyl-cysteine. Such agents also include various candidate agents (such as genistein) that have been derived from plants, which can be called flavones, flavonoids, biofla- vonoids, anthocyanins, polyphenols, or similar terms (the term flavonoid is preferred for use herein).

If desired, any such agent(s) can be incorporated into a zeaxanthin pre-treatment regimen, for testing in one or more classes of patients who will receive PDT.

In addition, the pre-loading regimen described herein can be carried out in coordination with (such as simultaneously, sequentially, etc.) any other currently-known or hereafter-developed treatment for choroidal neovascularization, such as (i) the use of steroidal anti-inflammatory drugs, before and/or after a PDT session; and/or, (ii) the use of anti-angiogenesis drugs, such as VEGF blocker drugs, or other drugs (such as thalidomide, one of the most potent anti-angiogenesis drugs ever discovered; its ability to block the growth of blood vessels was directly responsible for deformities involving stunted limbs, when pregnant women took it).

Photodynamic Therapy of Skin Tissue

Based on the research and results described herein, it has also been recognized by the Applicant that pretreatment with a xanthin carotenoid (preferably zeaxanthin) is also highly likley to improve the outcomes of one or more types of photodynamic therapy, carried out on the skin. These types of therapy, which can use selected types of lights (mainly lasers or ultraviolet lamps) to activate injectable or in some cases skin-permeating drugs, are sometimes used to treat skin disorders, such as psoriasis, eczema, and various forms of dermatitis (a descriptive term that is broad enough to cover nearly any type of rash, inflammation, or other visible skin problem). Such therapy may also be adapted to other uses, such as removal of tattoos, birthmarks, etc.

Most photodynamic treatment of skin is performed on epidermal tissue, which is the type of skin tissue that covers the large majority of the body. However, photodynamic therapy can also be adapted to treating lesions that may occur on epithelial skin (commonly known as "mucous membranes"), which is exposed and accessible in the lips, mouth, genitals.

This does not assert that all known types of photodynamic therapy of skin will indeed be improved by pretreatment using zeaxanthin, or some other xanthin carotenoid. Instead, it asserts that:

(i) essentially any type of photodynamic treatment of skin using light-activated drugs should be evaluated, in animal tests and/or human clinical trials, to determine whether that particular type of treatment will receive significant benefits from a pretreatment using zeaxanthin (or, if desired, any other xanthin carotenoid);

(ii) the likelihood is believed and anticipated to be high that at least some such skin treatments will be benefited by zeaxanthin or possibly other xanthin pretreatments; and, (iii) any potential risks to patients, from such pretreatments, are only very minor and minimal, and should not discourage or impede such tests.

When used to improve the benefits of photodynamic therapy on skin tissue, it is preferred that any such testing commence at pretreatment dosage levels of at least 20 mg/day, and dosages being tested preferably should range up to about 50, 80, or even 100 mg/day, rather than testing lower levels such as 3 mg/day. Nevertheless, at least some patients (such as patient who have low body weight, and who suffer from chronically low carotenoid intake) are likely to benefit from even relatively low dosages, such as 3 or 5 mg/day.

The following examples provide additional information to support various teachings, assertions, and conclusions herein.

EXAMPLES

Example 1

Treatment of Male in His Late 70's

An adult male, age 78 at the time, was suffering from wet macular degeneration. He was told that he did not have much time left with the residual vision he still had, and he was advised by his ophthalmologist to get his financial and legal affairs in order, while he still had as much eyesight left as possible.

This patient subsequently met and spoke with the Applicant herein, since the patient had learned that the Applicant was involved in founding a company that sells zeaxanthin, for treating macular degeneration. The Applicant informed him that he had some contacts at the Wilmer Eye Institute, a world-famous eye care and research institute affiliated with the Johns Hopkins Medical School, in Baltimore, Md., and that he (the Applicant) had made a number of donations to support research there. The Applicant offered to make some calls in the patient's behalf, to see if he could be seen and treated soon, and the patient accepted that offer.

At about that time, the patient began taking zeaxanthin supplements. It is believed that his typical daily dosage was 20 milligrams, from two 10 milligram capsules per day, usually taken with meals. The patient is also believed to have taken various other nutritional supplements during the relevant span of time, although their full contents, dosages, and durations are not known.

According to notes created by the ophthalmologist at the Wilmer Institute, obtained by the Applicant with approval from the patient, the patient suffered from subfoveal CNV in his right eye. Contact lens biomicroscopic examination also showed subretinal fluid overlying fibrovascular tissue, with a subretinal hemorrhage. Repeat fluorescein angiography "showed occult with no classic neovascularization with hemorrhage." Because of the apparent and presumed recent disease progression, the right eye was treated with PDT, in July 2003. According to the patient, the ophthalmologist advised him that his course of treatment likely would require 5 or 6 verteporfin-laser treatments, over a span of up to about 2 years.

His left eye was similar in appearance but questionable in extent, and there was no proven disease progression. Therefore, the ophthalmologist recommended careful monitoring but no PDT at that time.

When the patient told the ophthalmologist that he was taking zeaxanthin, the ophthalmologist suggested that he should stop, because it likely would not do any good, and it might interfere with the treatment. Despite that advice, the patient continued taking zeaxanthin.

Three months after the PDT treatment, in October 2003, the patient was examined again by the same ophthalmologist. The written report states, "clearing of much of the subretinal hemorrhage along the nasal aspect of the posterior pole with no new subretinal fluid". The report also states, "fluorescein angiography was repeated to determine if any additional treatment might be indicated". It showed "no fluorescein leakage to suggest the need for any additional treatment at this time except at the inferonasal aspect of the treated area, and so I suggested that he return in three months to reevaluate this area carefully to determine if any further therapy might be indicated. Color fundus photographs also were obtained to help the compare to future visits and documented the biomicroscopic features described above."

As described by the patient, the ophthalmologist also told the patient that he (the ophthalmologist) was very surprised by how well the results had turned out. The ophthalmologist informed him that the results were much better than expected, and that instead of needing 5 or 6 treatments over the next 2 years, the patient likely would need only 1 or 2.

The report from the next followup visit, three months later, in January 2004, described, "clearing of the subretinal hemorrhage that was noted along the inferonasal aspect of the treated area". Another fluorescein angiogram was obtained, and showed, and it "still showed some increased staining in the area where the hemorrhage had cleared but I did not suspect there was additional growth of neovascularization so no additional treatment was done at this time."

The left eye "showed some questionable increased subretinal fibrosis and fluid so that fluorescein angiography was obtained in that eye and showed some questionable leakage suggestive of occult neovascularization. Therefore, I told him to return in three months to watch the left eye and consider photodynamic therapy if we see any progression". Color fundus photographs were taken again, to serve as comparisons for future visits.

Two months later, in March 2004, the right eye showed "no new leakage from CNV to suggest the need for any treatment". However, the left eye (which had not previously been treated with PDT) showed "new subretinal fluid and lipid in the posterior pole . . . and showing growth of choroidal neovascularization compared to January 2004." Therefore, PDT was performed on the left eye, in March 2004.

Three months later, the patient was seen again by the same ophthalmologist. The written report has not been seen by the Applicant, but the patient orally reported that the ophthalmologist said the results were good.

Example 2

Results of Zeavision Customer Survey

In the summer of 2004, the assignee company (ZeaVision LLC) began searching for customers who were: (i) taking zeaxanthin supplements they had purchased from ZeaVision, and (ii) had received one or more PDT treatments, for wet macular degeneration. They did this by sending postcards to customers, asking them to contact ZeaVision if they had received PDT treatment. Those customers who responded were briefly interviewed by phone by the customer support staff, who asked questions and filled in a worksheet that had been prepared to help guide the interviews.

Most of these patients with age-related eye problems are in their 70's or 80's. They could not always provide exact dates when talking from memory during a phone call, and no efforts were made to check their actual medical records, or to consult with the ophthalmologists who performed their PDT treatments. In addition, nearly all of these patients were taking one or more additional vitamin supplements, such as lutein, Coenzyme Q10, and/or the AREDS formulation (all of which are commonly recommended by friends, relatives, and physicians), and at least one patient (identified as patient FE, below) also received a steroid injection as part of his PDT therapy. Accordingly, these results do not attempt to eliminate the possible influence of such additional factors, and they do not approach the level of rigor or statistical certainty of a clinical trial.

Nevertheless, these results appear to clearly and directly support the Applicant's conclusions, as set forth above.

Responses from patients who had been taking zeaxanthin for at least a month prior to a PDT treatment include the following examples:

Patient MC had 1 PDT session before commencing ZX. Her condition did not stabilize, and she needed another PDT session. She began taking ZX before the second session, and after the second session, her doctor said she appeared to not need any more PDT sessions.

Patient FE began taking ZX in June 2004, and had his first and only PDT treatment about 2 months later. His results were good, and his doctor said he may not need to have any more treatments.

Patient BJM is a retired former nurse, who recognized the symptoms fairly rapidly when the vision in her left eye began to blur. She consulted a doctor promptly, rather than waiting for several weeks or months to see if the problem would go away. She was diagnosed with wet AMD in March, and had three PDT sessions in fairly rapid succession, beginning in April 2004, on her left eye only. She began taking 10 mg/day of ZX in May 2004, which was after her first treatment. Her ZX regimen began only a short time before her second treatment, and she was taking only 10 mg/day, rather than the recommended 20 mg/day dosage. By the time of her third treatment, in July 2004, she had been taking 10 mg/day for about 2 months. At that time, her doctor told her to continue whatever she was doing, because it appeared to be working. Although the extent of damage was not severe and her results were actually quite good, her ophthalmologist felt that one small patch in particular, near one edge of her macula, might receive some additional protection from an additional PDT treatment, so he performed another treatment in October 2004. In October 2004, the patient described her results as "super-good", and stated that her vision in her left eye is 20/30, while her vision in her right eye remains at 20/20. Her ophthalmologist told her that she is one of an "elite group" who is actually having their sight restored and improved, rather than merely having the degeneration slowed down, by the treatments. Her comments included, "I'm pleased with how great it's doing," and, "I will not stop taking zeaxanthin".

Patient AK began taking zeaxanthin in mid to late 2003, after a first PDT treatment had occurred in June 2003. Her second PDT treatment was in May 2004, after she had been taking ZX for some months. During a followup examination in late June 2004, the doctor said her eyes had gotten better, and appeared to be stable, and he told her to continue taking zeaxanthin. During her next visit in October 2004, the ophthalmologist said her eyes had stabilized, and instead of asking to see her again 3 months later, he said she should wait for 4 months before her next appointment. She was very pleased with the outcome, and commented, "I'll soon be 88, and if I live to be 100, I'll still be taking it."

Survey respondent OD stated that her father had PDT treatment on his right eye, after three months of taking ZX. The doctor, when informed of the ZX supplements, said to keep taking them, because the condition of his treated eye appeared to be stable.

In addition to the foregoing, several respondents who had wet macular degeneration leading to PDT treatments in one eye only, and dry macular degeneration in the other eye, stated that they were happy with and grateful for the zeaxanthin they were taking, because it appeared to be helping the eye with dry macular degeneration remain stable, or in some cases improve.

Thus, there has been shown and described novel means for increasing the safety and efficacy of treatments for unwanted blood vessel growth in retinas. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Algvere, P. V., et al, "Age-related maculopathy: pathogenetic features and new treatment modalities," *Acta Ophthalmol Scand* 80: 136-43 (2002)

Ambati, J., et al, "Age-related macular degeneration: Etiology, pathogenesis, and therapeutic strategies," *Surv Opthalmology* 2003 May; 48(3): 257-293

Bailey T A, et al, "Oxidative stress affects the junctional integrity of retinal pigment epithelial cells," *Invest Ophthalmol Vis Sci.* 2004 February; 45(2): 675-84

Beatty, S., et al, "The role of oxidative stress in the pathogenesis of age-related macular degeneration," *Surv Ophthalmol.* 2000 September-October; 45(2): 115-34

Bhosale, P., et al, "Identification and characterization of a Pi isoform of glutathione-S-transferase (GSTP1) as a zeaxanthin-binding protein in the macula of the human eye," prepublished online by *Journal of Biological Chemistry* (September 2004, www.jbc.org)

Fernandez, P., et al, "A multivitamin complex with lutein and glutathione reduces VEGF expression and MMP-2 activity in a murine model of retinal oxidative stress," Abstract number 1814/B625 (2004), posted on ARVO website, www.arvo.org Handelman, G. J., et al, "Carotenoids in the human macula and whole retina," *Invest. Ophthalmol. Vis. Sci.* 29: 850-855 (1988)

Hunt, D. W., et al, "Status of therapies in development for the treatment of age-related macular degeneration," *IDrugs* 6: 464-9 (2003)

Hutchings, H., et al, "Pigment epithelium-derived factor exerts opposite effects on endothelial cells of different phenotypes," *Biochem Biophys Res Commun.* 294: 764-9 (2002)

Krinsky, N. I., et al, *Carotenoids In Health And Disease* (Marcel Dekker, 2004)

Lee S J, et al, "Astaxanthin inhibits nitric oxide production and inflammatory gene expression by suppressing I(kappa)B kinase-dependent NF-kappaB activation," *Mol Cells.* 2003 Aug. 31; 16(1): 97-105

Ohgami K, et al, "Effects of astaxanthin on lipopolysaccharide-induced inflammation in vitro and in vivo," *Invest Ophthalmol Vis Sci.* 2003 June; 44(6): 2694-701

Perez-Vendrell A M, et al, "Influence of source and ratio of xanthophyll pigments on broiler chicken pigmentation and performance," *Poult Sci.* 2001 March; 80(3): 320-6

Schalch, W., "Carotenoids in the retina—a review of their possible role in preventing or limiting damage caused by light and oxygen," Emerit I., et al, Ed, *Free Radicals and Aging:* 280-298 (1992)

Schmidt-Erfurth, U., et al, "Influence of photodynamic therapy on expression of vascular endothelial growth factor (VEGF), VEGF receptor 3, and pigment epithelium-derived factor," *Invest Ophthalmol Vis Sci* 44: 4473-80 (2003)

Snodderly, D. M., "Evidence for protection against age-related macular degeneration by carotenoids and antioxidant vitamins," *Am J Clin Nutr* 62(Suppl): 1448S-61S (1995)

Snodderly, D. M., et al, "The macular pigment. I. Absorbance spectra, localization, and discrimination from other yellow pigments in primate retinas," *Invest Ophthalmol Vis Sci* 25: 660-673 (1984a)

Spaide, R. F., et al, "Combined photodynamic therapy with verteporfin and intravitreal triamcinolone acetonide for choroidal neovascularization," *Ophthalmology* 110: 1517-25 (2003)

Stahl, W., et al, "Carotenoids and protection against solar UV radiation," *Skin Pharmacol Appl Skin Physiol.* 2002 September-October; 15(5): 291-6

Stahl, W., et al, "Antioxidant activity of carotenoids," *Mol Aspects Med.* 2003 December; 24(6): 345-51

Tamai, K., et al, "Lipid hydroperoxide stimulates subretinal choroidal neovascularization in the rabbit," *Exp Eye Res.* 2002 February; 74(2): 301-8

Wachtlin, J., et al, "Long-term results after photodynamic therapy with verteporfin for choroidal neovascularizations secondary to inflammatory chorioretinal diseases," *Graefes Arch Clin Exp Ophthalmol: Oct.* 11, 2003

Wormald, R., et al, "Photodynamic therapy for neovascular age-related macular degeneration," *Cochrane Database Syst Rev.* 2003 (2): CD002030 (2003)

Wrona M, et al, "Cooperation of antioxidants in protection against photosensitized oxidation," *Free Radic Biol Med.* 2003 Nov. 15; 35(10): 1319-29

Wrona M, et al, "Zeaxanthin in combination with ascorbic acid or alpha-tocopherol protects ARPE-19 cells against photosensitized peroxidation of lipids," *Free Radic Biol Med.* 2004 May 1; 36(9): 1094-101

Zarbin, M. A., "Current concepts in the pathogenesis of age-related macular degeneration," *Arch Ophthalmol.* 2004 April; 122: 598-614

The invention claimed is:

1. A method for treating unwanted retinal blood vessel growth in a patient in need of such treatment, comprising the following steps:
    for at least a week prior to photodynamic therapy, orally administering at least 10 milligrams of zeaxanthin per day to the patient so as to increase macular pigment density in said patient, the zeaxanthin being provided in the form of the 3R-3R stereoisomer of zeaxanthin;
    prior to photodynamic therapy and after the oral administration of the zeaxanthin for a week, treating the patient with a second agent selected from the group consisting of anti-angiogenesis drugs and anti-inflammatory drugs, the treatment with the second agent being separate from the oral administration of the zeaxanthin; and,
    subjecting the patient to photodynamic therapy using a drug that is activated by a light source.

2. The method of claim 1, wherein subjecting the patient to the photodynamic therapy includes the following steps: (i) injecting into the patient a drug that will release a toxic or radical compound when activated by a light source; (ii) allowing sufficient time to pass for the drug to circulate into retinal blood vessels; and, (iii) shining a light source that will activate the drug into at least one eye of the patient.

3. The method of claim 1, wherein the drug for the photodynamic therapy is selected from the group consisting of verteporfin, and rostaporfin, which are effective in photodynamic therapy.

4. A method for treating unwanted retinal blood vessel growth in a patient in need of such treatment, comprising the following steps:
    for at least one week prior to photodynamic therapy, orally administering at least one xanthin carotenoid to the patient, at a dosage of at least 10 milligrams per day to cause deposition of the xanthin carotenoid in at least one type of ocular tissue;
    prior to photodynamic therapy and after the oral administration of the xanthin carotenoid for a week, treating the patient with a second agent selected from the group consisting of anti-angiogenesis drugs and anti-inflammatory drugs, the treatment with the second agent being separate from the oral administration of the xanthin carotenoid, and,
    subjecting the patient to photodynamic therapy using a drug that is activated by a light source.

5. The method of claim 4 wherein the xanthin carotenoid is selected from the group consisting of zeaxanthin, lutein, astaxanthin, and canthaxanthin.

6. The method of claim 4, wherein the drug for the photodynamic therapy is selected from the group consisting of verteporfin, and rostaporfin, which are effective in photodynamic therapy.

7. A method for enhancing photodynamic therapy benefits in a patient suffering from unwanted retinal blood vessel growth, comprising the step of:
    for at least one week prior to photodynamic therapy, orally administering to such patient at least one xanthin carotenoid at a dosage-duration regimen that has been shown in human clinical trials to improve the efficacy of photodynamic therapy when administered prior to photodynamic therapy; and
    prior to photodynamic therapy and after the oral administration of the xanthin carotenoid for a week, treating the patient with a second agent selected from the group consisting of anti-angiogenesis drugs and anti-inflammatory drugs, the treatment with the second agent being separate from the oral administration of the xanthin carotenoid.

8. The method of claim 7 wherein the xanthin carotenoid is selected from the group consisting of zeaxanthin, lutein, astaxanthin, and canthaxanthin.

9. The method of claim 7, wherein zeaxanthin is administered at dosages of at least about 3 milligrams per day.

10. The method of claim 1, wherein the drug for the photodynamic therapy is verteporfin.

11. The method of claim 4, wherein the drug for the photodynamic therapy is verteporfin.

12. The method of claim 7, wherein the drug for the photodynamic therapy is verteporfin.

* * * * *